(12) United States Patent
Greaves et al.

(10) Patent No.: US 10,772,823 B2
(45) Date of Patent: *Sep. 15, 2020

(54) MOLECULARLY IMPRINTED POLYMER FOR SELECTIVELY TRAPPING ODOROUS MOLECULES

(71) Applicant: L'ORÉAL, Paris (FR)

(72) Inventors: Andrew Greaves, Magny-le-hongre (FR); Franco Manfre, Le Perreux sur Marne (FR); Karsten Haupt, Compiègne (FR); Jeanne Bernadette Tse Sum Bui, Compiègne (FR)

(73) Assignee: L'OREAL, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 14/655,390

(22) PCT Filed: Dec. 16, 2013

(86) PCT No.: PCT/EP2013/076655
§ 371 (c)(1),
(2) Date: Jun. 25, 2015

(87) PCT Pub. No.: WO2014/102077
PCT Pub. Date: Jul. 3, 2014

(65) Prior Publication Data
US 2015/0320667 A1  Nov. 12, 2015

Related U.S. Application Data

(60) Provisional application No. 61/773,181, filed on Mar. 6, 2013.

(30) Foreign Application Priority Data

Dec. 26, 2012  (FR) ..................... 12 62780

(51) Int. Cl.
*A61Q 15/00* (2006.01)
*A61K 8/81* (2006.01)
(Continued)

(52) U.S. Cl.
CPC .......... *A61K 8/8158* (2013.01); *A61K 8/8147* (2013.01); *A61Q 15/00* (2013.01);
(Continued)

(58) Field of Classification Search
CPC ...................................... B01J 20/268
See application file for complete search history.

(56) References Cited

U.S. PATENT DOCUMENTS 3,792,068 A  2/1974  Luedders et al.
5,630,978 A  5/1997  Domb
(Continued)

FOREIGN PATENT DOCUMENTS

EP   0925776 A2 *  6/1999  ............... A61K 8/73
EP   0925776 A2    6/1999
(Continued)

OTHER PUBLICATIONS

Non-Final Office Action for co-pending U.S. Appl. No. 14/655,395 dated Jun. 17, 2016.
(Continued)

*Primary Examiner* — Michael M Dollinger
*Assistant Examiner* — Christina H. W. Rosebach
(74) *Attorney, Agent, or Firm* — The Marbury Law Group, PLLC

(57) ABSTRACT

The invention relates to the use of molecularly imprinted polymer(s) or MIPs, of odorous molecule(s), as deodorant agent in particular for selectively trapping molecules that are the cause of human body odour. More particularly by using MIPs which may be obtained via polymerization, preferably via radical polymerization, of a mixture of: i) optionally one
(Continued)

Figure 1:
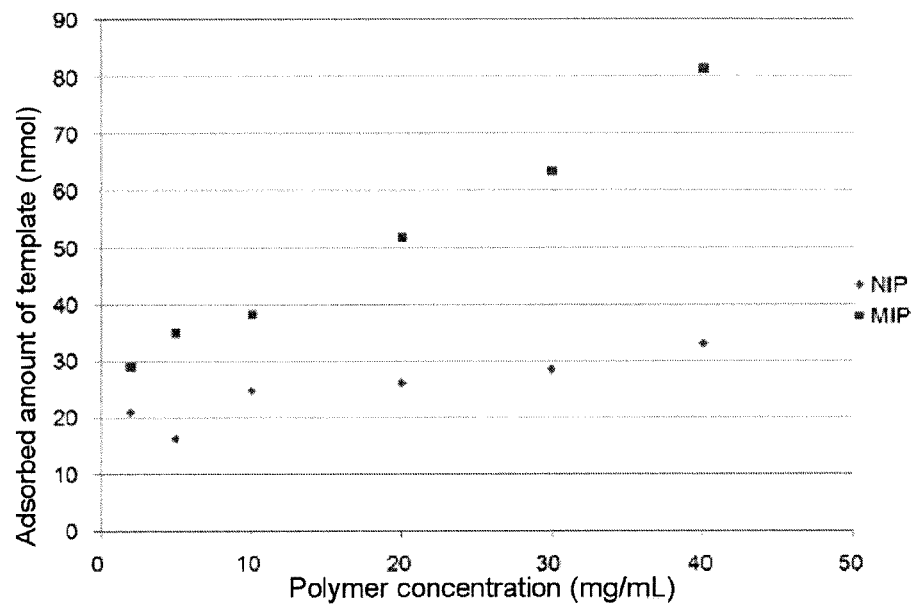

or more polymerization initiator(s); ii) one or more functional monomer(s); iii) one or more crosslinking agent(s); and iv) one or more porogenic solvent(s); it being understood that the polymerization a) or b) is performed in the presence v) of one or more "templates" of target molecule(s) responsible for human body odour. Another subject of the invention concerns a process for preparing MIPs as defined previously, MIPs obtained via this process, and a cosmetic composition comprising at least one MIP as defined previously. Unexpectedly, it appears that the MIPs make it possible to specifically trap precursors of odorous molecules and odorous molecules that may be used in cosmetic formulations, especially those that are the cause of the unpleasant odour of sweat.

17 Claims, 1 Drawing Sheet

(51) Int. Cl.
  *C08F 222/38* (2006.01)
  *C08F 222/10* (2006.01)
(52) U.S. Cl.
  CPC ...... *C08F 222/1006* (2013.01); *C08F 222/38* (2013.01); *A61K 2800/54* (2013.01); *C08F 222/102* (2020.02)

(56) References Cited

U.S. PATENT DOCUMENTS

| | | | |
|---|---|---|---|
| 5,932,199 A * | 8/1999 | Esser | A61K 8/0229 424/400 |
| 6,057,377 A | 5/2000 | Sasaki et al. | |
| 6,255,421 B1 | 7/2001 | Plochocka et al. | |
| 6,649,212 B2 | 11/2003 | Payne et al. | |
| 6,916,465 B2 | 7/2005 | Panzer et al. | |
| 7,820,770 B2 | 10/2010 | Schoeley et al. | |
| 8,114,921 B2 | 2/2012 | Poulton et al. | |
| 8,679,859 B2 | 3/2014 | Yan et al. | |
| 9,956,542 B2 | 5/2018 | Haupt et al. | |
| 10,335,355 B2 | 7/2019 | Greaves | |
| 2003/0020049 A1 | 1/2003 | Payne et al. | |
| 2005/0063928 A1 | 3/2005 | Withiam et al. | |
| 2005/0084464 A1 | 4/2005 | McGrath et al. | |
| 2005/0084474 A1 | 4/2005 | Wu et al. | |
| 2009/0148961 A1 * | 6/2009 | Luchini | B01D 15/34 436/518 |
| 2009/0291058 A1 | 11/2009 | Woodland et al. | |
| 2010/0048737 A1 * | 2/2010 | Wendel | A61K 8/8117 514/772.5 |
| 2010/0254932 A1 | 10/2010 | Benabdillah et al. | |
| 2012/0100358 A1 | 4/2012 | Haupt et al. | |
| 2013/0085186 A1 | 4/2013 | Wendel et al. | |
| 2014/0076346 A1 | 3/2014 | Bourdin et al. | |
| 2014/0205556 A1 | 7/2014 | Bourdin et al. | |
| 2016/0106652 A1 | 4/2016 | Greaves | |
| 2016/0143832 A1 | 5/2016 | Greaves | |

FOREIGN PATENT DOCUMENTS

| | | |
|---|---|---|
| EP | 0972512 A1 | 1/2000 |
| EP | 1146057 A1 | 10/2001 |
| EP | 1658863 A1 | 5/2006 |
| JP | 2000-086446 A | 3/2000 |
| WO | WO 2006062926 A1 * | 6/2006 ........... A61B 5/1172 |
| WO | 2008/034764 A2 | 3/2008 |
| WO | 2014/102078 A1 | 7/2014 |
| WO | 2014/102206 A1 | 7/2014 |
| WO | 2014/102209 A1 | 7/2014 |

OTHER PUBLICATIONS

International Search Report for PCT/EP2013/077787, dated Feb. 17, 2014.
International Search Report for PCT/EP2013/076659, dated Apr. 10, 2014.
International Search Report for PCT/EP2013/076655, dated Mar. 18, 2014.
International Search Report for PCT/EP2013/077790, dated Apr. 11, 2014.
First Office Action for counterpart Chinese Application No. 201380068610.6, dated Mar. 4, 2016. (English translation).
Second Office Action for counterpart Chinese Application No. 201380068610.6, dated Oct. 18, 2016. (English translation).
Sangeetha, Neralagatta M. et al., "Supramolecular gels: Functions and uses," Chemical Society Reviews, published Aug. 2005, pp. 821-836.
Final Office Action for copending U.S. Appl. No. 14/655,395, dated Feb. 9, 2017.
Non-Final Office Action for copending U.S. Appl. No. 14/655,381, dated Apr. 27, 2017.
Non-Final Office Action for copending U.S. Appl. No. 14/655,381, dated Feb. 16, 2018.
Obici, Silvana et al., "Central Administration of Oleic Acid Inhibits Glucose Production and Food Intake," Diabetes, vol. 51, Feb. 2002, pp. 271-275.
Non-Final Office Action for copending U.S. Appl. No. 14/655,386, dated Sep. 6, 2017.
Final Office Action for copending U.S. Appl. No. 14/655,386, dated May 4, 2018.
Non-Final Office Action for copending U.S. Appl. No. 14/655,395, dated Nov. 2, 2017.
Final Office Action for copending U.S. Appl. No. 14/655,381, dated Oct. 9, 2018.
Non-Final Office Action for copending U.S. Appl. No. 14/655,386, dated Nov. 1, 2018.
Co-pending U.S. Appl. No. 16/208,709, filed Dec. 4, 2018, entitled "Molecularly Imprinted Polymers of SOL-GEL Type and Their Use as Antidandruff Agent," Inventors: Andrew Greaves et al.
Final Office Action for copending U.S. Appl. No. 14/655,395, dated Sep. 4, 2018.
Vasapollo, G., et al., "Molecularly Imprinted Polymers: Present and Future Prospective," International Journal of Molecular Sciences, 2001, 12, pp. 5908-5945.
Mayes et al., "Molecularly imprinted polymers: useful materials for analytical chemistry?," trends in analytical chemistry, vol. 16, No. 6, 1997, pp. 321-332.
Mujahid et al., "Chemical Sensors Based on Molecularly Imprinted Sol-Gel Materials," Materials 2010, 3, pp. 2196-2217.
Non-Final Office Action for co-pending U.S. Appl. No. 16/208,109, dated Sep. 18, 2019.
Non-Final Office Action for co-pending U.S. Appl. No. 14/655,386, dated Jan. 22, 2020.
Non-Final Office Action for co-pending U.S. Appl. No. 14/655,381, dated Jul. 1, 2019.
Notice of Allowance for copending U.S. Appl. No. 14/655,381, dated May 5, 2020.
Final Office Action for copending U.S. Appl. No. 16/208,709, dated Jun. 5, 2020.

* cited by examiner

MOLECULARLY IMPRINTED POLYMER FOR SELECTIVELY TRAPPING ODOROUS MOLECULES

CROSS REFERENCE TO RELATED APPLICATIONS

This is a national stage application of PCT/EP2013/076655, filed internationally on Dec. 16, 2013, which claims priority to U.S. Provisional Application No. 61/773,181, filed on Mar. 6, 2013; as well as French Application 1262780, filed on Dec. 26, 2012, all of which are incorporated herein by reference in their entireties.

The invention relates to the use of molecularly imprinted polymers (or MIPs) for odorous molecule(s), as an agent for trapping molecules that are at the surface of keratin materials preferentially as deodorant agent, in particular for selectively trapping the molecules responsible for human body odour. The invention also relates to MIPs which trap odorous molecules, to a composition comprising the said polymers and to a process for preparing the said polymers.

In the cosmetic field, it is known practice to use in topical application deodorant products containing active substances of bactericidal type to reduce or even eliminate the generally unpleasant underarm odours [see for example Ullmann's Encyclopedia of Industrial Chemistry, "Skin Cosmetics", G. Schneider et al., http://onlinelibrary.wiley.com/doi/10.1002/14356007.a24_219/pdf, published online on 15 Jan. 2001, Wiley-VCH, DOI: 10.1002/14356007.a24_219, point 8 "deodorants and Antiperspirants" (2012)].

Eccrine or apocrine sweat has little odour when it is secreted. It is its degradation by bacteria via enzymatic reactions that produces malodorous compounds.

The compounds which contribute towards unpleasant underarm odours comprise malodorous steroids, branched, saturated and/or unsaturated aliphatic volatile fatty acids, especially of $C_2$-$C_{12}$, and sulfanylalkanol compounds (*Chem. Biodivers.*, 1, 1058-1072, (2004)). Certain precursors of odorous substances and the mechanisms of generation thereof are described in the scientific literature [see for example *Journal of Investigative Dermatology*, 130, 529-540, (2010); *Int. J. Cosmet. Sci.*, 26, 149-156, (2004)].

Deodorant active agents have the function of reducing or preventing the formation of unpleasant odours. The various systems proposed hitherto may be principally grouped into four major families i) to iv):

i) Bactericidal substances or substances that limit bacterial growth. Bactericides that destroy the resident bacterial flora. The most commonly used bactericides are Triclosan (2,4,4'-trichloro-2'-hydroxydiphenyl ether), chlorhexidine (1,6-bis(4-chlorophenylbiguanidino)hexane) and TTC (3,4,4'-trichlorocarbanilide). Among the substances that reduce bacterial growth, mention may be made of transition-metal chelating agents such as ethylenediaminetetraacetic acid (EDTA) or diethylenetriaminepentaacetic acid (DPTA);

ii) Substances that block the enzymatic reactions responsible for the formation of odorous compounds. Mention may be made of arylsulfatase inhibitors, 5-lipoxygenase inhibitors, aminoacylase inhibitors and β-glucuronidase inhibitors;

iii) Unpleasant odour absorbers which "capture" or reduce the volatility of odorous compounds. Odour absorbers that may be mentioned include zeolites and cyclodextrins. It is also known that certain types of solid particles may be used as deodorants, such as the metal oxide silicates of patent application US 2005/063 928; the metal oxide particles modified with a transition metal in patent applications US 2005/084 464 and US 2005/084 474, aluminosilicates such as those described in patent application EP 1 658 863, nanometric chitosan-based particles such as those described in patent U.S. Pat. No. 6,916,465; and iv) Antiperspirants, including aluminium and/or zirconium salts, which are the most commonly used as active agents.

The principle of action of these active agents is considered to be the formation of a gel in the sweat duct. This gel creates a plug that partially blocks the sweat pores. The flow of sweat is thus reduced. These aluminium salts also have intrinsic efficacy since they are antibacterial agents. They thus also play a direct role on the deodorant efficacy by reducing the number of bacteria responsible for the degradation of sweat.

These various treatments applied to the skin especially of the armpits have a tendency to cause skin impairments reflected by irregularities and inhomogeneities such as pigmentary marks in particular on asiatic skin, dyschromia or blackheads often caused by regrowth of the hair.

At the present time, on the deodorant/antiperspirant products market, one of the main challenges is that of finding a solution for masking these irregularities immediately and noticeably by the consumer on application, while conserving a natural visual aspect. Furthermore, it is important to achieve this objective with materials that are compatible in deodorant/antiperspirant formulations and that do not result in large traces on clothing in contact with the skin.

Compositions based on deodorant active agents and/or antiperspirant active agents which are intended to be applied to the armpits after hair removal, for the purpose of hiding the marks caused by the hair-removal treatment (razor, wax or hair-removing cream), redness and blackheads, have already been proposed in Japanese patent application JP 2000-086 446. These compositions contain body powders such as talc, and organic or mineral dyestuffs.

Makeup compositions in particular for the face, comprising an antiperspirant active agent and a silicone elastomer, for improving the remanence of the colour distribution after application over time and for giving the complexion a matt effect that lasts for several hours, are also known in patent application EP 0 972 512. These compositions may comprise fillers intended to give body or rigidity to the composition, and/or softness, a matt effect and uniformity to the makeup. Among these fillers, use may be made of interference particles such as nacres, which are iridescent particles that reflect light, such as natural mother-of-pearl, mica coated with titanium oxide, with iron oxide, with a natural pigment or with bismuth oxychloride, or coloured titanium mica.

The problem of hiding skin irregularities caused by the treatment of deodorant/antiperspirant products is not mentioned in these documents.

There thus remains a real need for deodorant/antiperspirant products and for hiding skin impairments virtually immediately and/or noticeably by the consumer on application and which leave virtually no marks or even which are free of visible marks on clothing that is in contact with the skin.

Molecularly imprinted polymers or MIPs are materials that are widely used for their applications in the fields of biotechnology, chemistry, chromatography, analytical chemistry and biology (*J. Mol. Recognit.*, 19, 106-180 (2006); Molecularly Imprinted Materials: Science and Technology, Marcel Dekker, NY, M. Yan and O. Ramstrom (2005)). The concept of molecular imprinting relates to Emil Fisher's famous "lock and key fit" principle known since 1894 for enzymes with their ligand (*Advances in Carbohydrate Chemistry and Biochemistry*, 1-20 (1994)). Molecular imprinting consists more specifically in making a polymer comprising specific cavities in the shape and size of a target molecule or "imprint", from a "template" molecule which serves as a model for the formation of recognition sites for the target molecule, having shape complementarity with the template serving for the formation of the said specific cavities.

Molecularly imprinted polymers are polymers prepared from functional monomers polymerized around the said template. The monomer is thus chosen so as to develop interactions with the said template, which may be covalent or non-covalent, usually non-covalent, i.e. a) hydrogen bonding, b) electrostatic interactions, c) ionic interactions, and nonionic interactions or even low-energy interactions such as d) Van der Waals bonds, e) hydrophobic-hydrophobic interactions and f) interactions of π-π stacking types. The polymerization then takes place in a porogenic solvent between the monomers complexed with the template and a crosslinking agent so as to form specific cavities. The bonds or interactions between the template and the monomers are then broken by means of suitable solvents to extract the template from the polymer support.

Extraction of the said template then leaves vacant recognition sites with high affinity for the target molecule. The shape and size of the imprint and the spatial arrangement of the functional groups within the recognition cavity are complementary to the template molecule and contain specific sites for interaction with the target molecule.

This type of selective trapping is described in several scientific articles (see for example *Analytical Chemistry* "Molecularly imprinted polymers: the next generation", 75(17), 376-383, (2003); *Chemical Engineering Journal*, "Selective separation of basic and reactive dyes by molecularly imprinted polymers (MIPs)", 149(1-3), 263-272, (2009), Kirk-Othmer Encyclopedia of Chemical Technology, "Molecular Imprinting", D. Spivak; accessible online since 25 Jun. 2010, DOI: 10.1002/0471238961.molespiv.a01; Molecularly Imprinted Polymers; B. R. Hart, K. J. Shea, http://onlinelibrary.wiley.com/doi/10.1002/0471216275.esm054/full, Encyclopedia of Polymer, Science and Technology, accessible online since 15 Jul. 2002; DOI: 10.1002/0471216275.esm054; J. Sep. Sci, M. Lasáková, P. Jandera, 32, 799-812; *Int. J. Mol. Sci.,* 7, 155-178 (2006)).

A study conducted on an MIP prepared using a testosterone-based template shows the importance of the positioning of the two hydrogen bonding donor and acceptor sites of this imprint molecule for the subsequent recognition of analogue molecules [see *J. Polymer Science: Part A: Polymer Chemistry*, S-H Cheong et al., 36, 1725 (1998)].

These MIPs have never been used as alternative deodorant agents.

The technical problems mentioned previously have been solved by using molecularly imprinted polymer(s) or MIPs as cosmetic agents for trapping molecule(s) that are at the surface of keratin materials and in particular the skin; more particularly via the use of molecularly imprinted polymer(s) or MIPs for odorous molecule(s) and/or molecule(s) responsible for body odour, as deodorant agents, i.e. agents for selectively trapping the odorous molecules and/or molecules responsible for body odour, preferentially human body odour. Preferentially, the MIP(s) used in the invention may be obtained by polymerization, preferably by radical polymerization, of a mixture of:
  i) optionally one or more polymerization initiator(s);
  ii) one or more functional monomer(s);
  iii) one or more crosslinking agent(s); and
  iv) one or more porogenic solvent(s);
it being understood that the polymerization is performed in the presence v) of one or more "template(s)" or target molecule(s) that are at the surface of keratin materials, the template(s) advantageously being chosen from odorous molecules and molecules responsible for human body odour such as those of sweat and sebum.

Another subject of the invention concerns a process for preparing MIPs as defined previously, and MIPs obtained via this process, it being understood that the said template(s) are other than testosterone or testosterone derivatives, and a cosmetic composition comprising at least one MIP as defined previously.

A subject of the invention is also a cosmetic process for treating keratin materials, especially the skin, against body odour and/or the molecule(s) responsible for odours, characterized in that at least one composition as defined is applied to the surface of the said materials.

It appears, unexpectedly, that MIPs can specifically trap molecules that are at the surface of keratin materials, especially the skin. More particularly, the MIPs of the invention can trap the precursors of odorous molecules and the odorous molecules, which may be used in cosmetic formulations, especially those which are the cause of unpleasant human body odour especially from sweat and sebum.

These MIPs can significantly reduce or eliminate human body odour, in particular underarm odour.

For the purposes of the present invention, and unless otherwise indicated, the following definitions apply:
  a "hydrocarbon-based chain" is "unsaturated" when it comprises one or more double bonds and/or one or more triple bonds;
  the "aryl" or "heteroaryl" radicals or the aryl or heteroaryl part of a radical may be substituted with at least one substituent borne by a carbon atom, chosen from:
    a $C_1$-$C_{16}$ and preferably $C_1$-$C_8$ alkyl radical optionally substituted with one or more radicals chosen from hydroxyl, $C_1$-$C_2$ alkoxy, $C_2$-$C_4$ (poly)hydroxyalkoxy, acylamino, amino substituted with two $C_1$-$C_4$ alkyl radicals, which may be identical or different, optionally bearing at least one hydroxyl group, or the two radicals possibly forming, with the nitrogen atom to which they are attached, a saturated or unsaturated, optionally substituted 5- to 7-membered and preferably 5- or 6-membered heterocycle optionally comprising another nitrogen or non-nitrogen heteroatom;
    a halogen atom such as chlorine, fluorine or bromine;
    a hydroxyl group;
    a $C_1$-$C_2$ alkoxy radical;
    a $C_2$-$C_4$ (poly)hydroxyalkoxy radical;
    an amino radical;
    nitro or nitroso;
    a 5- or 6-membered heterocycloalkyl radical;
    an optionally cationic 5- or 6-membered heteroaryl radical, preferentially imidazolium, optionally substituted with a ($C_1$-$C_4$)alkyl radical, preferentially methyl;
    an amino radical substituted with one or two $C_1$-$C_6$ alkyl radicals, which may be identical or different, optionally bearing at least: i) a hydroxyl group, ii) an amino group optionally substituted with one or two optionally substituted $C_1$-$C_3$ alkyl radicals, the said alkyl radicals possibly forming, with the nitrogen atom to which they are attached, a saturated or unsaturated, optionally substituted 5- to 7-membered heterocycle optionally comprising at least one other nitrogen or non-nitrogen heteroatom;

an acylamino radical (—N(R)—C(O)R') in which the radical R is a hydrogen atom or a $C_1$-$C_4$ alkyl radical optionally bearing at least one hydroxyl group and the radical R' is a $C_1$-$C_2$ alkyl radical;

a carbamoyl radical ((R)$_2$N—C(O)—) in which the radicals R, which may be identical or different, represent a hydrogen atom or a $C_1$-$C_4$ alkyl radical optionally bearing at least one hydroxyl group;

a carboxylic acid or ester radical, (—O—C(O)R') or (—C(O)OR'), in which the radical R' is a hydrogen atom or a $C_1$-$C_4$ alkyl radical optionally bearing at least one hydroxyl group, and the radical R' is a $C_1$-$C_2$ alkyl radical;

the carboxylic radical possibly being in acid or salified form (preferably with an alkali metal or a substituted or unsubstituted ammonium);

an alkylsulfonylamino radical (R'S(O)$_2$—N(R)—) in which the radical R represents a hydrogen atom or a $C_1$-$C_4$ alkyl radical optionally bearing at least one hydroxyl group and the radical R' represents a $C_1$-$C_4$ alkyl radical, or a phenyl radical;

an aminosulfonyl radical ((R)$_2$N—S(O)$_2$—) in which the radicals R, which may be identical or different, represent a hydrogen atom or a $C_1$-$C_4$ alkyl radical optionally bearing at least one hydroxyl group;

a cyano group (CN);

a (poly)haloalkyl group, preferentially trifluoromethyl ($CF_3$);

the cyclic or heterocyclic part of a non-aromatic radical of heterocycloalkyl type may be substituted with at least one substituent borne by a carbon atom, chosen from the groups:

hydroxyl;

$C_1$-$C_4$ alkoxy or $C_2$-$C_4$ (poly)hydroxyalkoxy;

alkylcarbonylamino ((RC(O)—NR'—) in which the radical R' is a hydrogen atom or a $C_1$-$C_4$ alkyl radical optionally bearing at least one hydroxyl group, and the radical R is a $C_1$-$C_2$ alkyl radical or an amino radical substituted with two $C_1$-$C_4$ alkyl groups, which may be identical or different, optionally bearing at least one hydroxyl group, the said alkyl radicals possibly forming, with the nitrogen atom to which they are attached, a saturated or unsaturated, optionally substituted 5- to 7-membered heterocycle optionally comprising at least one other nitrogen or non-nitrogen heteroatom;

alkylcarbonyloxy ((RC(O)—O—) in which the radical R is a $C_1$-$C_4$ alkyl radical or an amino radical substituted with two identical or different $C_1$-$C_4$ alkyl groups optionally bearing at least one hydroxyl group, said alkyl radicals possibly forming with the nitrogen atom to which they are attached a saturated or unsaturated, optionally substituted 5- to 7-membered heterocycle, optionally comprising at least one other nitrogen or non-nitrogen heteroatom;

alkoxycarbonyl ((RO—C(O)—) in which the radical R is a $C_1$-$C_4$ alkyl radical or an amino radical substituted with two identical or different $C_1$-$C_4$ alkyl groups optionally bearing at least one hydroxyl group, said alkyl radicals possibly forming with the nitrogen atom to which they are attached a saturated or unsaturated, optionally substituted 5- to 7-membered heterocycle, optionally comprising at least one other nitrogen or non-nitrogen heteroatom;

a cyclic or heterocyclic radical, or a non-aromatic part of an aryl or heteroaryl radical, may also be substituted with one or more oxo groups;

an "aryl" radical represents a fused or non-fused monocyclic or polycyclic group containing from 6 to 22 carbon atoms, and in which at least one ring is aromatic; in particular, the aryl radical is a phenyl, biphenyl, naphthyl, indenyl, anthracenyl or tetrahydronaphthyl and more preferentially phenyl or tetrahydronaphthyl;

a "heteroaryl" radical represents a 5- to 22-membered, monocyclic or polycyclic fused or non-fused group, comprising from 1 to 6 heteroatoms chosen from a nitrogen, oxygen, sulfur and selenium atom, at least one ring of which is aromatic; preferentially, a heteroaryl radical is chosen from acridinyl, benzimidazolyl, benzobistriazolyl, benzopyrazolyl, benzopyridazinyl, benzoquinolyl, benzothiazolyl, benzotriazolyl, benzoxazolyl, pyridinyl, tetrazolyl, dihydrothiazolyl, imidazopyridyl, imidazolyl, indolyl, isoquinolyl, naphthoimidazolyl, naphthoxazolyl, naphthopyrazolyl, oxadiazolyl, oxazolyl, oxazolopyridyl, phenazinyl, phenoxazolyl, pyrazinyl, pyrazolyl, pyrilyl, pyrazoyltriazyl, pyridyl, pyridinoimidazolyl, pyrrolyl, quinolyl, tetrazolyl, thiadiazolyl, thiazolyl, thiazolopyridinyl, thiazoylimidazolyl, thiopyrylyl, triazolyl, xanthyl and the ammonium salt thereof;

a "cyclic" radical is a "cycloalkyl" radical, i.e. a non-aromatic, monocyclic or polycyclic, fused or non-fused radical, containing from 5 to 22 carbon atoms, which may comprise one or more unsaturations, such as cyclohexyl or cyclopentyl;

a "heterocyclic" or "heterocycloalkyl" radical is a non-aromatic, monocyclic or polycyclic, fused or non-fused 5- to 22-membered radical, comprising from 1 to 6 heteroatoms chosen from nitrogen, oxygen, sulfur and selenium atoms, morpholinyl, thiomorpholinyl, piperidyl, piperazinyl, pyrrolidinyl, tetrahydrofuryl, tetrahydrothiophenyl, azepanyl, thioazepanyl; preferentially pyrrolidinyl and morpholino;

an "alkyl" radical is a linear or branched $C_1$-$C_{16}$ and preferably $C_1$-$C_8$ hydrocarbon-based radical; particularly $C_1$-$C_4$ such as methyl or ethyl;

an "alkenyl" radical is a linear or branched $C_2$-$C_{20}$ hydrocarbon-based radical comprising one or more conjugated or unconjugated double bonds, in particular a $C_4$-$C_{10}$ radical comprising one, two or three double bonds, preferentially only one double bond;

the term "optionally substituted" attributed to the alkyl or alkenyl radical means that the said alkyl radical may be substituted with one or more radicals chosen from the following radicals: i) hydroxyl, ii) $C_1$-$C_4$ alkoxy, iii) acylamino, iv) amino optionally substituted with one or two identical or different $C_1$-$C_4$ alkyl radicals, the said alkyl radicals possibly forming, with the nitrogen atom that bears them, a 5- to 7-membered heterocycle, optionally comprising another nitrogen or non-nitrogen heteroatom, v) phenyl, vi) ($C_1$-$C_6$)alkoxycarbonyl, vii) ($C_1$-$C_6$)alkylcarbonyloxy, viii) H—C(O)—O—;

an "alkoxy" radical is an alkyl-oxy or alkyl-O— radical for which the alkyl radical is a linear or branched $C_1$-$C_{16}$ and preferentially $C_1$-$C_8$ hydrocarbon-based radical; particularly $C_1$-$C_4$ such as methoxy or ethoxy, and when the alkoxy group is optionally substituted, this means that the alkyl group is optionally substituted as defined above;

a "(poly)haloalkyl" radical is an "alkyl" radical as defined previously, in which one or more hydrogen atoms are substituted or replaced with one or more halogen atoms such as the fluorine, chlorine or bromine atom; a polyhaloalkyl that may be mentioned is the trifluoromethyl group;

an "alkylthio" radical is a radical alkyl-S— for which the alkyl radical is a linear or branched $C_1$-$C_{16}$ and preferentially $C_1$-$C_8$ hydrocarbon-based radical; particularly $C_1$-$C_4$ such as methylthio or ethylthio, and when the alkylthio group is optionally substituted, this means that the alkyl group is optionally substituted as defined above;

an anionic counterion is organic or mineral, preferentially chosen from halide anions such as $Cl^-$, $Br^-$ or $I^-$, and organic anions such as mesylates;

when the expression "at least one" is used, "one or more" is implied;

the limit values delimiting the extent of a range of values are included in this range of values.

In the context of the present invention, the term "deodorant active agent" means any active agent which, by itself, has the effect of masking, absorbing, improving and/or reducing the unpleasant odour resulting from the decomposition of human sweat.

The term "antiperspirant active agent" means any substance which, by itself, has the effect of reducing the flow of sweat, of reducing the sensation on the skin of moisture associated with human sweat and of masking human sweat.

The "Supports" for the MIPs

The retention of the support for the MIPs with the said template is based on a molecular recognition mechanism in the functional monomer "pre-organized" and polymerized around the said template of odorous molecule(s) and/or of target molecule(s) responsible for human body odour.

More particularly, the MIP(s) according to the invention may be obtained from i) optionally one or more polymerization initiators; ii) one or more functional monomer(s); iii) optionally one or more crosslinking agent(s); iv) one or more porogenic solvent(s) in the presence v) of one or more template molecules for the odorous molecule(s) and/or target molecule(s) responsible for human body odour.

It is understood that ii) the functional monomer(s) may be of identical nature, i.e. acidic, basic, zwitterionic or neutral; or may be a mixture of monomers of different nature, i.e. neutral monomer(s)+basic monomer(s), neutral monomer(s)+acidic monomer(s), or basic monomer(s)+acidic monomer(s).

According to a preferred embodiment of the invention, the MIPs are composed of crosslinked organic polymers, i.e. they are obtained from functional monomer(s), and from crosslinking agent(s), which constitute the support.

These polymers may be prepared using the standard polymerization methods known to those skilled in the art.

Mention may be made of the following methods: anionic addition polymerization, bulk polymerization, cationic polymerization, chain growth polymerization, condensation polymerization, coordination polymerization, emulsion polymerization, living anionic polymerization, living polymerization, living cationic polymerization, living free radical polymerization, plasma polymerization, precipitation polymerization, radical polymerization, reversible addition-fragmentation chain transfer polymerization, ring-opening polymerization, solution polymerization, step-growth polymerization, suspension polymerization, photo-induced polymerization.

Mention may also be made of initiator-free polymerization methods such as ultrasonic polymerization (*Macromolecules,* 1992, 25 (24), pp. 6447-6454; *Journal of Polymer Science*: Part A: *Polymer Chemistry*, Vol. 44, 5445-5453 (2006); *British Polymer Journal*, Volume 23, Issue 1-2, pages 63-66, 1990)). These methods have the advantage of avoiding the residual initiators in the final product.

Polymerization:

According to a particularly advantageous variant, the polymerization method used for manufacturing the MIPs according to the invention is radical polymerization from a polymerization initiator.

i) The Polymerization Initiator and Polymerization Temperature with the Imprint Molecule These polymerizations may be performed in the presence of a polymerization initiator.

The term "polymerization initiator" in particular means free-radical initiators generated via thermal routes or from light sources (see for example *Macromol. Rapid Commun.* Christian Decker, 23, 1067-1093 (2002); Encyclopedia of Polymer Science and Technology, "photopolymerisation free radical" http://onlinelibrary.wiley.com/doi/10.1002/0471440264.pst490/pdf; ibid, "photopolymerisation, cationic", http://onlinelibrary.wiley.com/doi/10.1002/0471440264.pst491/pdf; *Macromol. Symp.* 143, 45-63 (1999)). These photoactive compounds are not chemical oxidizing agents such as peroxides including hydrogen peroxide or systems for generating hydrogen peroxides. Two major families may be distinguished: that of type I in which the photoactive compounds bring about, under irradiation, a unimolecular cleavage of the covalent bond to give a free radical compound also symbolized by a "point", and of type II in which the photoactive compounds, under irradiation, lead to a bimolecular reaction in which the photoactive compounds in their excited state interact with a second molecule (or co-initiator) to generate free radicals.

More particularly, the radical initiators are chosen from the compounds of formula (A), (B), (C), (D), (E) or (F) and also the organic or mineral acid salts thereof, optical or geometrical isomers and tautomers thereof, and solvates thereof such as hydrates:

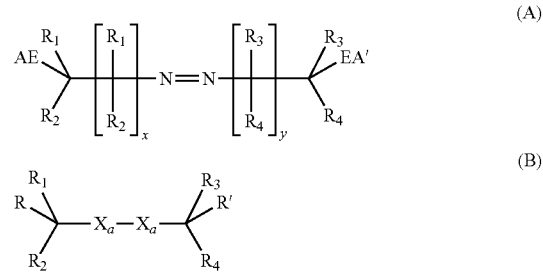

in which formula (A) or (B):

$R_1$, $R_2$, $R_3$ and $R_4$, which may be identical or different, represent a hydrogen atom or an optionally substituted linear or branched ($C_1$-$C_8$)alkyl or linear or branched ($C_1$-$C_8$)alkoxy group; an optionally substituted aryl such as phenyl;

or alternatively $R_1$ and $R_2$ and/or $R_3$ and $R_4$ form, together with the carbon atoms that bear them, a 3- to 7-membered optionally substituted (hetero)cycloalkyl, particularly $(C_3-C_6)$cycloalkyl such as cyclohexyl;

preferably, $R_1$, $R_2$, $R_3$ and $R_4$, which may be identical or different, represent a hydrogen atom or a linear or branched $(C_1-C_6)$alkyl group;

x and y, which may be identical or different, represent an integer between 0 and 6 inclusively, and preferably x and y=0;

R and R', which may be identical or different, preferably identical, represent i) a radical EA or EA' as defined previously, or a group chosen from ii) optionally substituted linear or branched $(C_1-C_3)$alkyl, iii) optionally substituted aryl, iv) optionally substituted aryl$(C_1-C_8)$ alkyl, or alternatively R with $R_1$ and/or R' with $R_3$ form, together with the carbon atom that bears them, a group $C(X^1)$ and $R_2$ and $R_4$ being as defined previously or $R_2$ and $R_4$, which may be identical or different, represent a group $R_5-(X^2)_w-$ in which w is 0 or 1, $R_5$ represents a hydrogen atom, a linear or branched $(C_1-C_8)$alkyl group, an optionally substituted (hetero)aryl group such as phenyl or a (hetero)cycloalkyl group optionally substituted especially with a $(C_1-C_6)$alkyl group such as cyclohexyl optionally substituted with a $(C_1-C_6)$ alkyl group and $X^2$ is as defined below;

EA and EA', which may be identical or different, preferably identical, represent an electron-withdrawing group, which is preferably electron-withdrawing via a mesomeric effect -M, such as cyano, $-C(X^1)-X^2-R_a$, phosh(on)ate, sulf(on)ate, nitro or nitroso; more particularly EA=EA'=CN;

$X_a$, which may be identical or different, represent a heteroatom chosen from oxygen and sulfur, a group —C(O)—O— or —O—C(O)—, a group —O—C(O)—O— or —O—C(O)—O—; preferably, $X_a$ represent an oxygen atom;

$X^1$ and $X^2$, which may be identical or different, representing a heteroatom chosen from oxygen, sulfur and amino N(R'') with R'' being a hydrogen atom or a linear or branched $(C_1-C_6)$alkyl group; preferably, $X^1$ and $X^2$ represent an oxygen atom;

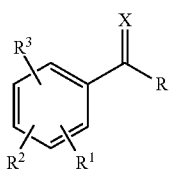
(C)

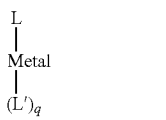
(D)

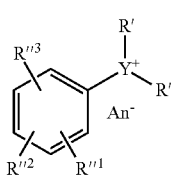
(E)

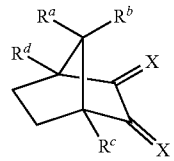
(F)

in which formula (C), (D), (E) or (F):

R represents a group chosen from:

i) $(C_1-C_{10})$alkyl, which is optionally substituted, preferably with one or more atoms or groups chosen from halogen, hydroxyl, $(C_1-C_{10})$alkoxy, 5- to 10-membered (hetero)cycloalkyl such as morpholinyl, and amino $R_aR_bN-$ with $R_a$ and $R_b$, which may be identical or different, representing a hydrogen atom or a $(C_1-C_{10})$ alkyl group or alternatively $R_a$ and $R_b$ form, together with the nitrogen atom that bears them, a heteroaryl or heterocycloalkyl group such as morpholino;

ii) $(C_1-C_{10})$alkoxy, which is optionally substituted, preferably with the same substituents as for i) $(C_1-C_{10})$ alkyl;

iii) hydroxyl;

iv) optionally substituted (hetero)aryl such as optionally substituted phenyl of formula

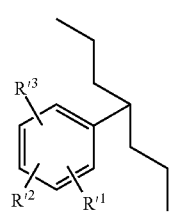
(C')

with $R'^1$, $R'^2$ and $R'^3$, which may be identical or different, being as defined for $R^1$, $R^2$ and $R^3$ and ⌇⌇ representing the point of attachment to the rest of the molecule;

v) (hetero)cycloalkyl which is optionally substituted, preferably with a hydroxyl group or a $(C_1-C_{10})$alkyl group;

vi) $R^4-(X)_n-C(X)-(X)_{n'}-$ with $R^4$ representing an optionally substituted $(C_1-C_{10})$alkyl, optionally substituted (hetero)aryl such as optionally substituted phenyl of formula (C'), or optionally substituted (hetero)cycloalkyl group, n and n', which may be identical or different, being equal to 0 or 1;

vii) $R_cR_dP(X)-$ with $R_c$ representing an optionally substituted $(C_1-C_{10})$alkyl or optionally substituted (hetero) aryl group, and $R_d$ representing an optionally substituted (hetero)aryl group;

viii) or alternatively $R^1$ with R ortho to the group $C(X)-R$ or R'' and $R''^1$ ortho to the group $R'-Y'-R''$ form, together with the atoms that bear them, a (hetero) cycle fused to the phenyl or (hetero)aryl fused to the phenyl, optionally substituted, especially on the non-aromatic part, with one or more oxo or thioxo groups; preferably $R^1$ with R ortho to the group $C(X)-R$ form, together with the atoms that bear them and the fused phenyl ring, an anthraquinone group (G):

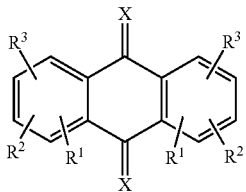

(G)

R¹, R² or R³, which may be identical or different, represent i) a hydrogen atom, ii) a halogen atom such as chlorine, iii) an optionally substituted $(C_1-C_{10})$alkyl group, iv) $(C_1-C_{10})$alkoxy optionally substituted especially with a hydroxyl group, v) optionally substituted (hetero)aryl, vi) optionally substituted (hetero)cycloalkyl, vii) carboxyl, viii) cyano, ix) nitro, x) nitroso, xi) —$S(O)_p$—OM with p equal to 1 or 2, M representing a hydrogen atom or an alkali metal or alkaline-earth metal, xii) $R^4R^5N$—, xiii) $R^4$—$(X)_n$—$C(X)$—$(X)_{n'}$— with $R^4$, n and n' as defined previously, $R^5$ is as defined for $R^4$ or alternatively $R^4$ and $R^5$ form, together with the nitrogen atom that bears them, an optionally substituted heterocycloalkyl or heteroaryl such as morpholino, which may be identical or different, being equal to 0 or 1, xiv) hydroxyl, or xv) thiol;

R'¹, R"² or R"'³, which may be identical or different, are as defined for R¹, R² and R³, are preferably chosen from a hydrogen atom or $R^4$—Y— with $R^4$ being as defined previously and preferably a phenyl group;

or alternatively contiguous R and R¹ form, together with the carbon atoms that bear them, an optionally unsaturated and optionally substituted (hetero)cycloalkyl group, preferably cycloalkyl that is optionally substituted in particular with one or more oxo groups and/or optionally fused with an aryl group such as benzo;

or alternatively two contiguous substituents R¹, R² and/or R'¹, R'² together form a group derived from maleic anhydride such as —C(X)—X—C(X)—;

X, which may be identical or different, represents an oxygen or sulfur atom or a group $NR^5$ with $R^5$ as defined previously, preferably representing a hydrogen atom or a $(C_1-C_{10})$alkyl group; more particularly, X represents an oxygen atom;

Y is as defined for X, and preferably Y represents a sulfur atom;

Metal represents a transition metal such as iron or chromium, preferably Fe, the said metal possibly being cationic, in which case the initiator of formula (D) comprises a number of anionic counterions An⁻ as defined previously, for affording the molecule electrical neutrality;

L and L', which may be identical or different, representing a transition metal ligand preferably chosen from the following electron donors: C(X) with X as defined previously, cyano CN, $(C_1-C_6)$alkenyl, optionally substituted (hetero)aryl such as bipyridyl, amines such as the amines $R^4R^5R^6N$ with $R^4$ and $R^5$ as defined previously and $R^6$ representing a hydrogen atom, or a group as defined for $R^4$, phosphine $R^4R^5R^6P$ such as tri(hetero)arylphosphine, (hetero)cycloalkyl which is preferably unsaturated, such as cyclopentadiene, carbene such as arduengo carbenes, q representing an integer inclusively between 1 and 6, for affording the metal complex stability, i.e. so as to obtain an electron number around the Metal equal to 16 or 18 electrons (it is also referred to as a coordination sphere with 16 or 18 electrons);

R' and R", which may be identical or different, represent an optionally substituted (hetero)aryl group;

An⁻ represents an anionic counterion as defined previously, preferably chosen from $(Hal)_6P^-$, or $(Hal)_6Sb^-$, with Hal, which may be identical or different, representing a halogen atom such as fluorine; and $R^a$, $R^b$, $R^c$ or $R^d$, which may be identical or different, represent a hydrogen atom or a $(C_1-C_{10})$alkyl group.

According to a preferred embodiment of the invention, the initiator(s) are chosen from the following compounds:

| Designation | CAS No. |
|---|---|
| Benzophenone | 0000119-61-9 |
| Benzophenone, 2-methyl- | 0000131-58-8 |
| Benzophenone, 4-methyl- | 0000134-84-9 |
| Benzoic acid, 2-benzoyl-, methyl ester | 0000606-28-0 |
| Benzophenone, 3-methyl- | 0000643-65-2 |
| 2-Isopropylthioxanthone | 0005495-84-1 |
| Benzoic acid, 4-(dimethylamino)-, ethyl ester | 0010287-53-3 |
| Benzoic acid, p-(dimethylamino)-, 2-ethylhexyl ester | 0021245-02-3 |
| Poly(ethylene glycol) bis(p-dimethylaminobenzoate) | 0071512-90-8 |
| Phosphine oxide, diphenyl(2,4,6-trimethylbenzoyl)- | 0075980-60-8 |
| 4-Isopropylthioxanthone | 0083846-86-0 |
| 1-[4-(2-Hydroxyethoxy)phenyl]-2-hydroxy-2-methyl-1-propan-1-one | 0106797-53-9 |
| 1-Butanone, 2-(dimethylamino)-1-[4-(4-morpholinyl)phenyl]-2-(phenylmethyl)- | 0119313-12-1 |
| 1-Butanone, 2-(dimethylamino)-2-[(4-methylphenyl)methyl]-1-[4-(4-morpholinyl)phenyl]- | 0119344-86-4 |
| Phenyl bis(2,4,6-trimethylbenzoyl) phosphine oxide | 0162881-26-7 |
| Benzene, (1-methylethenyl)-, homopolymer, ar-(2-hydroxy-2-methyl-1-oxopropyl) derivs. | 0163702-01-0 |
| Oxyphenylacetic acid 2-[2-oxo-2-phenylacetoxyethoxy]ethyl ester | 0211510-16-6 |
| Oxyphenylacetic 2-[2-hydroxyethoxy]ethyl ester | 0442536-99-4 |
| Poly[oxy(methyl-12-ethanediyl)], α-[4-(dimethylamino)benzoyl-ω-butoxy | 0223463-45-4 |
| 1-(4-[(4-Benzoylphenyl)thio]phenyl)-2-methyl-2-[(4-methylphenyl)sulfonyl]-1-propan-1-one | 0272460-97-6 |
| 2-Hydroxy-1-(4-(4-(2-hydroxy-2-methylpropionyl)benzyl)phenyl)-2-methyl-2-propanone | 0474510-57-1 |
| Diester of carboxymethoxybenzophenone and polytetramethylene glycol 250 | 0515136-48-8 |
| Diester of carboxymethoxybenzophenone and polyethylene glycol 200 | 0515136-49-9 |
| Poly(oxy-1,4-butanediyl), α-[2-[(9-oxo-9H-thioxanthenyl)oxy]acetyl]-ω-[[2-[(9-oxo-9H-thioxanthenyl)oxy]acetyl]]- | 0813452-37-8 |
| 4-(2-Hydroxyethoxy)phenyl-(2-hydroxy-2-propyl) ketone | 0106797-53-9 |

![structure]

(Methylamino)diethane-2,1-diylbis(4-dimethylamino amino benzoate)
Riboflavin

| | |
|---|---|
| Anthraquinone, 2-ethyl- | 0000084-51-5 |
| Thioxanthen-9-one, 2-chloro- | 0000086-39-5 |
| Benzophenone, 4,4'-bis(diethylamino)- | 0000090-93-7 |
| Phosphine oxide, triphenyl- | 0000791-28-6 |
| Methanone, (1-hydroxycyclohexyl)phenyl- | 0000947-19-3 |
| Methanone, phenyl(2,4,6-trimethylphenyl)- | 0000954-16-5 |
| Glyoxylic acid, phenyl-, ethyl ester | 0001603-79-8 |
| 4-Phenylbenzophenone | 0002128-93-0 |
| Benzoic acid, 2-(dimethylamino)ethyl ester | 0002208-05-1 |
| Acetophenone, 2,2-diethoxy- | 0006175-45-7 |
| 1H-Imidazole, 2-(2-chlorophenyl)-1-[2-(2-chlorophenyl)-4,5-diphenyl-2H-imidazol-2-yl]-4,5-diphenyl- | 0007189-82-4 |

| Designation | CAS No. |
|---|---|
| 1-Propanone, 2-hydroxy-2-methyl-1-phenyl- | 0007473-98-5 |
| d,l-Camphorquinone | 0010373-78-1 |
| Glyoxylic acid, phenyl-, methyl ester | 0015206-55-0 |
| 2,2-Dimethoxy-2-phenylacetophenone | 0024650-42-8 |
| Phenoxyethyl acrylate | 0048145-04-6 |
| Methyl 2-benzoylbenzoate | 0000606-28-0 |
| 2-Benzyl-2-(dimethylamino)-4-morpholinobutyrophenone | 0119313-12-1 |
| Ethyl 4-dimethylaminobenzoate | 0010287-53-3 |
| Iodonium, bis(4-methylphenyl)-, hexafluorophosphate(1⁻) | 0060565-88-0 |
| Bis(4-tert-butylphenyl)iodonium hexafluorophosphate | 0061358-25-6 |
| 1,2-Propanedione, 1-phenyl-, 2-[O-(ethoxycarbonyl)oxime] | 0065894-76-0 |
| Benzoic acid, 4-(dimethylamino)-, 2-butoxyethyl ester | 0067362-76-9 |
| Sulfonium, diphenyl[(phenylthio)phenyl]-, hexafluorophosphate(1⁻) (1:1) | 0068156-13-8 |
| 1-Propanone, 1-[4-(1,1-dimethylethyl)phenyl]-2-hydroxy-2-methyl- | 0068400-54-4 |
| Sulfonium, diphenyl[4-(phenylthio)phenyl]-, (OC-6-11)-hexafluoroantimonate(1-) (1:1) | 0071449-78-0 |
| Iodonium, bis(4-dodecylphenyl)-, (OC-6-11)-hexafluoroantimonate(1⁻) (1:1) | 0071786-70-4 |
| 1-Propanone, 2-methyl-1-[(4-methylthio)phenyl]-2-(4-morpholinyl)- | 0071868-10-5 |
| 1H-Azepine-1-propanoic acid, hexahydro-, 2,2-bis[[(1-oxo-2-propenyl)oxy]methyl]butyl ester | 0073003-78-8 |
| Bis(4-diphenylsulfonium)phenyl sulfide bis(hexafluorophosphate) | 0074227-35-3 |
| Diphenyl[(phenylthio)phenyl]sulfonium hexafluorophosphate | 0075482-18-7 |
| Anthracene, 9,10-dibutoxy | 0076275-14-4 |
| 2,4-Diethyl-9H-thioxanthen-9-one | 0082799-44-8 |
| 9H-Thioxanthene-2-carboxylic acid, 9-oxo-, ethyl ester | 0083817-60-1 |
| Methanone, [4-[(4-methylphenyl)thio]phenyl]phenyl- | 0083846-85-9 |
| Phosphinic acid, phenyl(2,4,6-trimethylbenzoyl)-, ethyl ester | 0084434-11-7 |
| Triphenylsulfonium hexafluorophosphate (mono + di)salts | 0086481-78-9 |
| Tryptophan | 000073-22-3 |
| Thiobis(4,1-phenylene)- S,S,S',S'-tetraphenyldisulfonium bishexafluoroantimonate | 0089452-37-9 |
| Triphenylsulfonium hexafluorophosphate | 0104558-95-4 |
| Bis (η-(5)-cyclopentadienyl)-bis(2,6-difluoro-3-[pyrrol-1-yl]-phenyl)titanium | 0125051-32-3 |
| 1-Chloro-4-propoxythioxanthone | 0142770-42-1 |
| Phosphine oxide, bis(2,6-dimethoxybenzoyl)(2,4,4-trimethylpentyl)-(9Cl) | 0145052-34-2 |
| Iodonium, [4-(1-methylethyl)phenyl](4-methylphenyl)-, tetrakis(2,3,4,5,6-pentafluorophenyl)borate(1-) (1:1) | 0178233-72-2 |
| 4,4'-Bis(methylethylamino)benzophenone | 0194655-98-6 |
| Iodonium, (4-methylphenyl)[4-(2-methylpropyl)phenyl]-, hexafluorophosphate(1-) | 0344562-80-7 |
| 9H-Thioxanthenium, 10-[1,1'biphenyl]-4-yl-2-(1-methylethyl)-9-oxo, hexafluorophosphate | 0591773-92-1 |
| Oxirane, 2-methyl-, polymer with oxirane, 2-benzoylbenzoate | 1003557-16-1 |
| {a-4-(Dimethylamino)benzoylpoly(oxyethylene)-poly[oxy(1-methylethylene)]-poly(oxyethylene)}4-(dimethylamino)benzoate | 1003557-17-2 |
| 1,3-Bis({a-2-(phenylcarbonyl)benzoylpoly[oxy(1-methylethylene)]}oxy)-2,2-bis({a-2-(phenylcarbonyl) benzoylpoly[oxy(1-methylethylene)]}oxymethyl)propane | 1003567-82-5 |
| 1,3-Bis({a-[1-chloro-9-oxo-9H-thioxanthen-4-yl]oxy]acetylpoly[oxy(1-methylethylene)]}oxy)-2,2-bis({a-[1-chloro-9-oxo-9H-thioxanthen-4-yl]oxy]acetylpoly[oxy(1-methylethylene)]}oxymethyl)propane | 1003567-83-6 |
| 1,3-Bis({-4-(dimethylamino)benzoylpoly[oxy(1-methylethylene)]}oxy)-2,2-bis({-4-(dimethylamino)benzoylpoly[oxy(1-methylethylene)]}oxymethyl) propane | 1003567-84-7 |
| Poly(oxy-1,2-ethanediyl), a-[2-(4-chlorobenzoyl)benzoyl]-w-[[2-(4-chlorobenzoyl)benzoyl]oxy]- | 1007306-69-5 |
| 2-Propenoic acid, 1,1'-[9-[[(1-fluoro-9-oxo-9H-thioxanthen-4-yl)oxy]methyl]-7,12-dimethyl-3,6,8,11,13,16-hexaoxaoctadecane-1,18-diyl] ester | 1253390-33-8 |
| 2,3-Dihydroxy-6-(2-hydroxy-2-methyl-1-oxopropyl)-1,1,3-trimethyl-3-[4-(2-hydroxy-2-methyl-1-oxopropyl)phenyl]-1H-indene | |
| 2-Hydroxy-[4'-(2-hydroxypropoxy)phenyl]-2-methylpropanone | |

| Designation | CAS No. |
|---|---|
| Polyethylene glycol (200) di(β-4[p-acetylphenyl]piperazine) propionate | |
| Polyethylene glycol (200) di(β-4[4-(2-dimethylamino-2-benzyl)butanoylphenyl]piperazine) propionate | |
| Bis(4-tert-butylcyclohexyl) peroxydicarbonate | 15520-11-3 |
| Diiisobutyryl peroxide | 3473-84-1 |
| Cumyl peroxyneodecanoate | 26748-47-0 |
| Bis(3-methoxybutyl) peroxydicarbonate | 52238-68-3 |
| 1,1,3,3-tetramethylbutyl peroxyneodecanoate | 51240-95-0 |
| Cumyl peroxyneoheptanoate | 130097-36-8 |
| t-amyl peroxyneodecanoate | 68299-16-1 |
| Dimistyryl peroxydicarbonate | 53220-22-7 |
| 1,1,3,3-tetramethylbutyl peroxypivalate | 22288-41-1 |
| tert-butyl peroxyneoheptanoate | 26748-38-9 |
| t-amyl peroxypivalate | 29240-17-3 |
| Bis(3,5,5-trimethylhexanoyl) peroxide | 3851-87-4 |
| Dilauroyl peroxide | 105-74-8 |
| Didecanoyl peroxide | 762-12-9 |
| Dibenzoyl peroxide | 94-36-0 |
| t-butyl peroxy-2-ethylhexanoate | 3006-82-4 |
| t-butyl peroxydiethylacetate | 2550-33-6 |
| t-butyl peroxyisobutyrate | 109-13-7 |
| t-butyl peroxybenzoate | 614-45-9 |
| Dicumyl peroxide | 80-43-3 |

Photoactive compounds that may also be mentioned include dyes known as "photosensitizing dyes" such as ethyl eosin, eosin Y, fluorescein, rose bengal, methylene blue, erythrosine, phloxime, thionine, riboflavin and methylene green.

According to a particular embodiment of the invention, a combination of initiator compounds is used.

According to a particularly advantageous embodiment of the invention, the free-radical initiator(s) used for the polymerization are of formula (A) or (B) as defined previously. More particularly, the initiator(s) are of formula (A).

According to another particular embodiment of the invention, the free-radical initiator(s) that are useful for the polymerization are of formula (B) as defined previously, preferentially with Xa representing a group O, R with $R_1$ and R' with $R_3$ form, together with the carbon atom that bears them, an oxo group and $R_2$ and $R_4$ represent a group $R_5$—$(O)_w$— in which w is 1, $R_5$ representing an optionally substituted (hetero)aryl group such as phenyl or a (hetero)cycloalkyl group optionally substituted especially with a $(C_1-C_6)$alkyl group such as cyclohexyl optionally substituted with a $(C_1-C_6)$alkyl group. Preferentially, the radical initiator(s) are the initiator below:

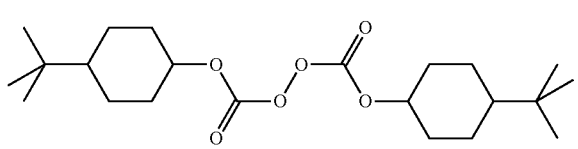

According to a particular embodiment of the invention, the radical polymerization initiator is AIBN (azobisisobutyronitrile). This initiator generates free radicals i) under the influence of heat at a temperature of greater than or equal to 45° C., preferentially at a temperature of greater than or equal to 55° C., more particularly at 60° C.; and/or ii) photochemically.

According to another particular embodiment of the invention, the radical polymerization initiator is ABDV (2,2'-azobis(2,4-dimethylvaleronitrile)). This agent may be used under thermally "milder" polymerization conditions. Preferentially, when ABDV is used, the polymerization process is performed at a temperature of greater than or equal to 28° C. and preferentially at a temperature of greater than or equal to 35° C., such as at 40° C. Preferably, the polymerization is performed at a temperature between 0° C. and 80° C. and more particularly between 25° C. and 70° C.

According to a particular embodiment, the polymerization is performed at low temperature, i.e. at a temperature of between 1 and 5° C.

ii) The Functional Monomer

The quality of the imprints formed depends especially on the strength of the interactions existing between the imprint molecule and the functional monomer(s) in the prepolymerization mixture. Four types of approach may particularly be used for preparing the MIPs of the invention:

a) Covalent Approach

According to a variant of the invention, the assembly or preorganization of the template with the polymerizable functional monomer takes place via the covalent approach. This is a method known to those skilled in the art (see for example G. Wulff, et al., *Affinity Chrom. and Related Techniques*, Elsevier Scientific Publishing Company, Amsterdam, 207, (1982); ibid, *Pure Appl. Chem.*, 54, 2093 (1982); ibid, *Tetrahedron Lett.* 4329 (1973); K. J. Shea, E. A. Thompson, *J. Org. Chem.* 43 4255 (1978); J. Damen, D. C. Neckers, *J. Org. Chem.* 45, 1382 (1980)). In a first stage, the template is covalently bonded to at least one polymerizable group which will be the point of attachment of the target molecule. When the polymerization is complete, the bonding between the template and the monomer is broken, preferably by hydrolysis or by a specific reaction for cleaving the targeted bond. The covalent bond(s) are capable of forming again when the polymer is in contact with the target molecule or an analogue having the same function.

More particularly, the functional monomer(s) used in this approach are of formula (C1) below:

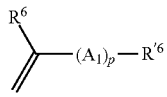

and also optical or geometrical isomers thereof, and organic or mineral acid or base salts thereof, and also solvates such as hydrates;

in which formula (C1):

$A_1$ represents a divalent group which allows π electrons to pass, such as the ethylene group —$CH_2$=$CH_2$—, or (hetero)arylene, especially phenylene;

p represents an integer between 0 and 5 inclusive; in particular p=0 or 1, preferentially p=1;

$R^6$ represents a hydrogen atom or a linear or branched ($C_1$-$C_8$)alkyl group, optionally substituted preferably with one or more halogen atoms such as a fluorine atom;

$R'^6$ represents a group chosen from i) amino NH—$R_d$ with $R_d$ representing a hydrogen atom or a linear or branched ($C_1$-$C_6$)alkyl group, ii) hydroxyl, iii) thiol, iv) linear or branched ($C_1$-$C_8$)alkyl, substituted with one or more groups chosen from —OH and —SH, preferably with several —OH or —SH groups, particularly with two —OH groups; v) —C($X^1$)—$X^2$-Alk-N(H)—$R_d$ with Alk representing a linear or branched ($C_1$-$C_8$) alkylene group, such as ethylene, and $R_d$ as defined previously; and vi) —B(O$R_d$)$_2$ with $R_d$, which may be identical or different, as defined previously; and $X^1$ and $X^2$ being as defined previously, preferably $X^1$=O or NH and $X^2$=O.

Preferentially, the template(s) of the invention comprise at least one functional group of the following types:

alcohol —OH, thiol —SH, amino —$NH_2$, particularly OH; which is capable of forming with the monomer, after removal of water or of $H_2S$, a (thio)ester —X—C(X)— or (thio)amide —N(H)—C(X)— function with X as defined previously;

(thio)aldehyde or (thio)ketone and amine capable of forming with the monomer a Schiff's base bearing an imine function —CH=N— or >C=N—, respectively.

More particularly, the templates of the invention comprising groups of the 1,2- or 1,3-diol type such as mannose, glyceric acid, amino acids and α-hydroxycarboxylic acids are capable of forming boronic esters in the presence of imprint molecules [the polymerization method used is identical to that described by Wulff et al., A. Sarhan, G. Wulff, *Makromol. Chem.* 183, 85 (1982)].

More particularly, the monomer(s) used in the invention are chosen from the following monomers:

| Type of bond | No. | Monomer structure |
|---|---|---|
| ketal | (a) | ![structure with OH, OH] |
| Schiff's base | (b) | $CH_2$=C($CH_3$)—C(O)—N(H)—($CH_2$)$_2$—$NH_2$ |
| Boronic ester | (c) | ![structure with B(OH)$_2$] |

The MIPs obtained from these monomers may be prepared according to the processes known to those skilled in the art [see for example for K. J. Shea et al. *J. Am. Chem. Soc.* 113, 4109 (1991), ibid, *Macromol.*, 22 4303 (1989); ibid, *Macromol.* 23, 4497(1990); (c): G. Wulff et al. *J. Liq. Chromatogr.* 13, 2987 (1990); ibid, *Makromol. Chem.* 188, 731 (1987), ibid, *Makromol. Chem.*, 178, 2799 (1977)].

The target compounds or templates imprinted via this method are preferably chosen from compounds bearing alcohol, aldehyde, ketone, amine and carboxylic acid function(s).

b) Non-Covalent Approach

According to another variant of the invention, the assembly or preorganization of the template with the polymerizable functional monomer takes place via a non-covalent approach. This is a method which is also known to those skilled in the art [see for example R. Arshady, K. Mosbach, *Macromol. Chem. Phys.*, 182, 687, (1981); O. Ramström, et al. *Tetrahedron: Asymmetry*, 5, 649 (1994); B. Sellergren, *Chirality* 1, 63 (1989)]. This printing method involves interactions between the monomer and the prepolymerization complex template, which are of low energy relative to the energy of covalent bonds*. These interactions are of hydrogen bonding, electrostatic or ionic bonding, 11-17 stacking or Van Der Waals bonding type.

* Nature of the Interaction Energy: hydrogen bonding 25-40 kJ·mol$^{-1}$, dipole-dipole 25-40 kJ·mol$^{-1}$, ionic 250-1050 kJ·mol$^{-1}$ vs. covalent bonding 670-3360 kJ·mol$^{-1}$ In particular, the functional monomer(s) used in the non-covalent approach according to the invention are functional monomers bearing —$X^2H$, —C($X^1$)—$X^2H$, phosph(on)ate, sulf(on)ate, —N(H)—$R_b$, —C($X^1$)—N(H)—$R_b$ (hetero)aryl or (hetero)cycloalkyl functions, with $X^1$ and $X^2$ as defined previously, preferably $X^1$=O or NH, and $X^2$=O, and $R_b$ represents a hydrogen atom or a linear or branched ($C_1$-$C_8$)alkyl group. More particularly, the monomer(s) used in this approach are of formula (C2) below:

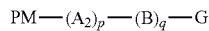

and also optical or geometrical isomers thereof, and organic or mineral acid or base salts thereof, and also solvates such as hydrates;

in which formula (C2):

PM represents the polymerizable part chosen from PM1 and PM2:

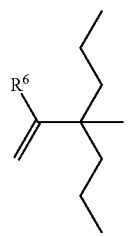

PM1

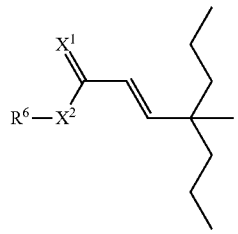

PM2

$A_2$ represents a divalent group which allows π electrons to pass, such as the ethylene group —$CH_2$=$CH_2$—, or (hetero)arylene, especially phenylene, or alternatively $A_2$ represents a —$CH_2$— group, in which case p is 1;

B represents a heteroatom or a group $X^1$ as defined previously;

p represents an integer between 0 and 10 inclusive; in particular p=0 or 1, preferentially p=0;

q is 0 or 1, preferably, when $A_2$ represents a —$CH_2$— group and when p is 1, then q is 1, otherwise q is 0;

$R^6$ represents a hydrogen atom or a linear or branched ($C_1$-$C_8$)alkyl group, optionally substituted preferably with one or more halogen atoms such as a fluorine atom or a group (G3) such as carboxyl;

G represents an acidic, basic or neutral group chosen from i) amino $N(R'')_2$ with R'', which may be identical or different, being a hydrogen atom or a linear or branched ($C_1$-$C_6$)alkyl group, ii) cyano, iii) (G1), iv) (G2) and v) (G3) below:

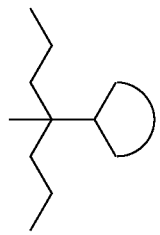

(G1)

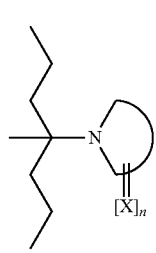

(G2)

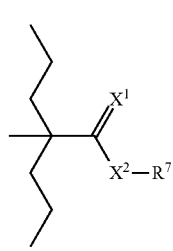

(G3)

with (G1) representing i) a heteroaryl group which is preferably 5- or 6-membered, comprising at least one nitrogen atom in the aromatic ring, such as 2-pyridyl, 4-pyridyl, 4-imidazolyl and 5-imidazolyl, or ii) an aryl group such as phenyl which is optionally substituted, preferably with a ($C_1$-$C_6$)alkyl group;

(G2) representing a heterocycloalkyl group which is preferably 5- or 6-membered, such as pyrrolidinone;

X representing an oxygen or sulfur atom, preferably oxygen;

n representing an integer inclusively between 1 and 4, preferably n=1 or 2;

$R^7$ representing a hydrogen atom or a linear or branched ($C_1$-$C_8$)alkyl group, which is optionally substituted, preferably with one or more groups chosen from a) sulf(on)ate, b) phosph(on)ate, c) —$X^1$—H, d) —C($X^1$)—$X'^2$—H, e) amino —$N(R''')_2$ and f) ammonium —$N^+(R''')_3$ with R''', which may be identical or different, being a hydrogen atom or a linear or branched ($C_1$-$C_6$)alkyl group, optionally substituted with an amino group;

$X^1$ and $X^2$ being as defined previously, preferably $X^1$=O or NH, and $X^2$=O and $X'^1$ and $X'^2$ being as defined previously for $X^1$ and $X^2$;

} represents the point of attachment of the groups (PM1), (PM2), (G1), (G2) and (G3) to the rest of the molecule of formula (C2).

More particularly, the monomer(s) used for synthesizing the MIPs of the invention are of formula (C2) with PM=PM1 and G=G3.

Even more particularly, the monomer(s) used in the invention are chosen from the acidic, neutral and basic monomers in the table below:

|  | Monomer name | No./Abbreviation | Structure |
|---|---|---|---|
| Acidic monomer | Acrylic acid | 1 | $H_2C=CH-C(O)-OH$ |
|  | Methacrylic acid | 2/MAA | $CH_2=C(CH_3)-C(O)-OH$ |
|  | 3-(3-Pyridyl)acrylic acid | 3 | (3-pyridyl acrylic acid structure) |
|  | 3-(4-Pyridyl)acrylic acid | 3' | (4-pyridyl acrylic acid structure) |
|  | 2-(Methacryloyloxy)ethyl phosphate | 4/MEP | $CH_2=C(CH_3)-C(O)O-(CH_2)_2-OP(O)OH_2$ |
|  | 2-Acrylamido-2-methyl-1-propenesulfonic acid | 4'/AMPSA | $CH_2=CH_2-C(O)NH-C(CH_3)_2-CH_2-S(O)_2OH$ |
|  | Itaconic acid | 4" | $HO-C(O)-CH_2-C(=CH_2)-C(O)-OH$ |
|  | para-Vinylbenzoic acid | 5 | (para-vinylbenzoic acid structure) |
| Basic monomer | 3-vinylpyridine | 6/3-VP | (3-vinylpyridine structure) |
|  | 4-vinylpyridine | 6'/4-VP | (4-vinylpyridine structure) |
|  | 4-vinylpyridine associated with cobalt $Co^{2+}$ | 6-Co | (4-vinylpyridine-Co²⁺ complex structure) |
|  | 2-vinylpyridine | 7/2-VP | (2-vinylpyridine structure) |
|  | para-aminostyrene | 8 | (para-aminostyrene structure) |
|  | 4-(5)-vinylimidazole | 9 | (4-(5)-vinylimidazole structure) |
|  | Ethylurocanic ester | 9' | (ethylurocanic ester structure) |
|  | 1-vinylimidazole | 9" | (1-vinylimidazole structure) |
|  | diethylaminoethyl methacrylate | 10/DEAEM | $CH_2=C(CH_3)-C(O)O-(CH_2)_2N(CH_2CH_3)_2$ |
|  | 2-aminoethyl methacrylate | 10'/AEM | $CH_2=C(CH_3)-C(O)O(CH_2)_2N(H)CH_2CH_3$ |
|  | N,N,N-trimethylammonium ethylmethacrylate | 10" | $CH_2=C(CH_3)-C(O)O-(CH_2)_2N^+(CH_3)_3$, $Q^-$ with Q- an anionic counterion such as halide |
|  | Aminoethylmethacrylamide | 10''' | $CH_2=C(CH_3)-C(O)-NH-(CH_2)_2-NH_2$ |
|  | Diethylaminoethyl acrylate | 10'''' | $CH_2=CH-C(O)O-(CH_2)_2N(CH_2CH_3)_2$ |
|  | 2-aminoethyl acrylate | 10''''' | $CH_2=CH-C(O)O(CH_2)_2N(H)CH_2CH_3$ |
|  | N,N,N-trimethylammonium | 10'''''' | $CH_2=CH-C(O)O-(CH_2)_2N^+(CH_3)_3$, $Q^-$ with |

| Monomer name | No./Abbreviation | Structure |
|---|---|---|
| ethylacrylate Aminoethylacrylamide | 10''''' | Q- an anionic counterion such as halide $CH_2=CH-C(O)-NH-(CH_2)_2-NH_2$ |
| 4-Styrylamidine derivative with R = H, methyl or ethyl | 15 | |
| N,N'-diethyl-4-styrylamidine (N,N'-dimethyl)-4-styrylamidine with R, which may be identical or different, representing H, methyl or ethyl | 11 | |
| amine derivative of benzamidine | 11' | |
| Neutral monomer acrylamide | 12/AA or AAm | $H_2C=CH-C(O)-NH_2$ |
| methacrylamide | 12' | $H_2C=C(CH_3)-C(O)-NH_2$ |
| methyl methacrylate | 12'' | $H_2C=C(CH_3)-C(O)-O-CH_3$ |
| methylacrylate | 12''' | $H_2C=CH-C(O)-O-CH_3$ |
| vinylpyrrolidone | 13 | |
| 2-hydroxyethyl methacrylate | 14/HEMA | $CH_2=C(CH_3)-C(O)O-(CH_2)_2-OH$ |
| acrylonitrile | 14'/AN | $CH_2=CH-CN$ |
| 2-hydroxyethyl acrylate | 14'' | $CH_2=CH-C(O)O-(CH_2)_2-OH$ |
| styrene | 15 | |
| ethylstyrene | 16 | |
| 1-allyl-2-(thio)urea | 16 | $H_2C=CH-CH_2-N(H)-C(X)-NH_2$ with X representing a sulfur or oxygen atom S or O |

The MIPs obtained from these monomers may be prepared according to the processes known to those skilled in the art [see for example for 1: K. Sreenivasan, *J. Appl. Polymer Sci.*, 80, 2795 (2001); 2: J. Matsui et al., *Anal. Chem.*, 67, (1995); B. Sellergren et al., *J. Am. Chem. Soc.*, 110, 5853 (1988) and D. A. Spivak, K. J. Shea., *Macromolecules*, 31, 2160 (1998); 4: A. Kugimiya et al., *J. Chromatogr. A*, 938, 131 (2001); 5 and 6 and 6': J. Matsui et al., *Anal. Chim. Acta*, 343, 1 (1997); 6 X. Huang et al., *J. Mol. Recogn.*, 16, 406 (2003); J. Bastide et al., *Anal. Chim. Acta*, 542, 97 (2005); 6-Co: J. Hedin-Dahlstrom et al., *J. Org. Chem.*, 71, 4845 (2006); 7: J. Bastide et al., *Anal. Chim. Acta*, 542, 97 (2005), K. Möller, et al., *J. Chromatogr. B*, 811, 171 (2004), Z. Xu et al., *J. Pharm. and Biomed. Analysis*, 41, 701 (2006); 9: A. Kugimiya, *Anal. Chim. Acta*, 564, 179 (2006), Y. Kawanami et al., *J. Mol. Catalysis A: Chem.*, 145, 107 (1999); 10: S. A. Piletsky et al., *Biosensors and Bioelectronics*, 10, 959 (1995); 11 and 11': J-M. Kim et al., *Macromol. Chem. and Phys.*, 202, 1105, (2001), J-Q. Liu, G. Wulff, *Angew. Chem. Int. Ed. Engl.*, 43, 1287 (2004); 12: T. L. Zhang at al., *Anal. Chim. Acta*, 450, 53 (2001), C. Yu, K. Mosbach., *J. Org. Chem.*, 62, 4057 (1997), J. Xie et al., *J. Chromatogr. A*, 934, 1 (2001); 13: C. Baggiani et al., *J. Chromatogr. A*, 1117, 74 (2006); 14: B. Dirion et al., *J. Am. Chem. Soc.*, 125, 15101(2003); 15: A. G. Strikovsky et al., *J. Am. Chem. Soc.*, 122, 6295 (2000); 16: A. Kugimiya, H. Takei, *Anal. Chim. Acta*, 564, 179 (2006)].

The functional groups of the monomers are chosen such that the selectivity towards the target molecule or the template is optimized according to the functional groups of the said target molecule. In other words, the template and the functions of the monomer are chosen via the complementarity approach so that the preorganization takes place with the target molecule. For example, if either the monomer or template bears a primary or secondary amine or hydroxyl group, it is necessary that, facing it, the template or the monomer, respectively, bear a complementary function capable of creating a hydrogen bond, for example a carboxyl or thiocarboxyl group such as —O—H/////O=C< or —O—H/////S=C< or —N(H)—H/////O=C< or —N(H)—

H/////S=C<. If the template comprises hydrophobic parts of aryl type, it is necessary that, facing it, the functional monomer comprise an aryl group such as phenyl so as to form interactions of pi-stacking type, if the aliphatic parts of the template are of long-chain aliphatic type especially comprising more than 10 carbon atoms, it is necessary that, facing it, there should be a functional monomer comprising at least one aliphatic group especially also comprising more than 10 carbon atoms so as to form interactions of hydrophobic type.

Thus, according to a preferred embodiment of the invention, the monomers used for the MIPs of the invention are acidic.

According to another particular embodiment of the invention, the monomers used for the MIPs of the invention are basic.

According to yet another particular embodiment of the invention, the monomers used for the MIPs of the invention are neutral.

According to yet another particular embodiment of the invention, the monomers used for the synthesis of MIPs correspond to a mixture of different monomers such as: acidic monomers+neutral monomers or basic monomers with neutral monomers.

According to another particular embodiment of the invention, the polymerization method used for manufacturing the MIPs is radical polymerization of monomers bearing an acrylate or acrylate-based function known to those skilled in the art (see for example "acrylic ester polymers"; "radical polymerisation" Encyclopedia of Polymer Science and Technology, John Wiley & Sons Inc.
http://onlinelibrary.wiley.com/doi/10.1002/0471440264.pst007.pub2/pdf; and
http://onlinelibrary.wiley.com/doi/10.1002/0471440264.pst306/pdf respectively).

c) Semi-Covalent Approach

According to another variant of the invention, the assembly or preorganization of the template with the polymerizable functional monomer takes place via a semi-covalent approach. This is a method which is also known to those skilled in the art (see for example J. U. Klein et al., *Angew. Chem. Intl.*, 38, 2057 (1995)). The semi-covalent route consists in covalently forming imprints and in re-uptaking the template or analogue molecule non-covalently. Conventionally, the template comprises at least one nucleophilic group Nu, in which case the functional monomer comprises at least one electrophilic group E generating one or more covalent bonds $T_a$ after the attack of the nucleophilic part on the electrophilic part. Alternatively, the template comprises at least one group E and the functional monomer comprises at least one group Nu.

By way of example, the covalent bonds $T_a$ that may be generated between the template and the functional monomer are listed in Table A, starting with condensation of electrophiles with nucleophiles:

TABLE A

| Electrophiles E | Nucleophiles Nu | Covalent bonds $T_a$ |
| --- | --- | --- |
| Activated esters* | Amines | Carboxamides |
| Acyl azides** | Amines | Carboxamides |
| Acyl halides | Amines | Carboxamides |
| Acyl halides | Alcohols | Esters |
| Acyl cyanides | Alcohols | Esters |
| Acyl cyanides | Amines | Carboxamides |
| Alkyl halides | Amines | Alkylamines |
| Alkyl halides | Carboxylic acids | Esters |

TABLE A-continued

| Electrophiles E | Nucleophiles Nu | Covalent bonds $T_a$ |
| --- | --- | --- |
| Alkyl halides | Thiols | Thioesters |
| Alkyl halides | Alcohols | Ethers |
| Sulfonic acids and salts thereof | Thiols | Thioethers |
| Sulfonic acids and salts thereof | Carboxylic acids | Esters |
| Sulfonic acids and salts thereof | Alcohols | Ethers |
| Anhydrides | Alcohols | Esters |
| Anhydrides | Amines | Carboxamides |
| Aryl halides | Thiols | Thioethers |
| Aryl halides | Amines | Arylamines |
| Aziridines | Thiols | Thioethers |
| Carboxylic acids | Amines | Carboxamides |
| Carboxylic acids | Alcohols | Esters |
| Carbodiimides | Carboxylic acids | N-Acylureas or anhydrides |
| Diazoalkanes | Carboxylic acids | Esters |
| Epoxides | Thiols | Thioethers |
| Haloacetamides | Thiols | Thioethers |
| Imide esters | Amines | Amidines |
| Isocyanates | Amines | Ureas |
| Isocyanates | Alcohols | Urethanes |
| Isothiocyanates | Amines | Thioureas |
| Maleimides | Thiols | Thioethers |
| Sulfonic esters | Amines | Alkylamines |
| Sulfonic esters | Thiols | Thioethers |
| Sulfonic esters | Carboxylic acids | Esters |
| Sulfonic esters | Alcohols | Ethers |
| Sulfonyl halides | Amines | Sulfonamides |

*the activated esters of general formula —CO-Part with Part representing a leaving group such as optionally substituted oxysuccinimidyl, oxybenzotriazolyl or aryloxy;
**the acyl halides may rearrange to give isocyanates.

These reactions are known to those skilled in the art and are described in the literature. Reference may be made to the book Advanced Organic Chemistry (ISBN 0-471-60180-2).

This approach is particularly appreciated when the imprint molecule or the template is of the steroid family or conjugated sulfate forms thereof.

d) Approach Via Coordination Bonds with Transition Metals

According to another variant of the invention, the assembly or preorganization of the template with the polymerizable monomer takes place via an approach of coordination bonding with transition metals. This is a method which is also known to those skilled in the art (see for example Y. Fujii et al., *J. Chem. Soc., Chem. Commun.*, 415 (1985); P. K. Dhal, F. H. Arnold, *J. Am. Chem. Soc.*, 113, 7417 (1991); D. R. Shnek et al., *Langmuir*, 10, 2382 (1994); S. D. Plunkett, F. H. Arnold, *J. Chromatogr. A*, 708, 19 (1995); S. Striegler, *Tetrahedron*, 57, 2349 (2001); G. H. Chen et al., *Nat. Biotechnol.*, 15, 354 (1997); S. Striegler, *Tetrahedron*, 57, 2349 (2001); S. Striegler, M. Dittel, *J. Am. Chem. Soc.*, 125, 11518 (2003)). The functionalized complexes are composed of at least one metal ion and of at least one polymerizable ligand, forming a ternary complex via coordination bonds with the target molecule to be imprinted.

The terms "metal complex" and "coordination compounds" mean systems in which the metal ion, the central atom, is chemically bonded to one or more electron donors (ligands). A ligand comprising various coordinating groups (capable of coordinating with a metal) gives metal compounds corresponding to principles of a coordination sphere with a predetermined number of electrons (internal complexes or chelates)—see Ullmann's Encyclopedia of Industrial Chemistry, "*Metal complex dyes*", 2005, p. 1-42.

The monomers according to the invention are particularly chosen from the derivatives of formula (C2) as defined previously comprising at least one electron-donating group such as —OH, —SH or -J(R)$_2$ with J representing a nitrogen or phosphorus atom, R representing a hydrogen atom or a linear or branched (C$_1$-C$_6$)alkyl group, preferably R=H; the said electron-donating group(s) being complexed to one or more transition metals; the said transition metal(s) also possibly being stabilized by complexation with one or more ligands L bearing at least one electron-donating group such as amino, phosphino, hydroxyl or thiol, or the ligand is a "persistent" carbene particularly of Arduengo type (imidazol-2-ylidenes); preferentially, the ligand is a phosphine such as triphenylphosphine or bi/tridentate bearing an amino and/or hydroxyl group.

More particularly, the MIP(s) of the invention are prepared from monomers of formula (C2) as defined previously in which G represents the radical (G4) below:

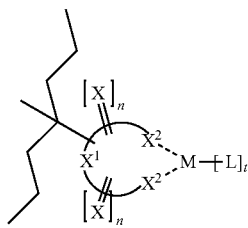

(G4)

with
M representing a transition metal such as Co, Cu, Fe, Zn, Mn, Ti, and V, preferably Co and Cu;
L representing a ligand complexed to the metal as defined previously;
- - - representing
X representing an oxygen or sulfur atom, preferably oxygen,
n and t, which may be identical or different, representing an integer inclusively between 0 and 4, preferably n=1 or 2;
X$^1$ and X$^2$ being as defined previously, or alternatively X$^1$ represents a bond;
( representing a linear or branched (C$_1$-C$_6$)alkylene group, preferably of C$_2$ such as ethylene; and
} representing the point of attachment of the group (G4) to the rest of the molecule of formula (C2).

More particularly, the transition metal used is cobalt, preferably Co(III). This metal is particularly appreciated when an amino acid derivative is used as imprint molecule or template. Even more particularly, mention may be made of copper, preferably Cu(II). This metal is particularly appreciated when a sugar derivative, especially a glucose derivative, is used as imprint molecule or template.

Preferentially, in the invention, the support for the MIPs of the invention consists of functional monomer(s) which are preferably prepared with a functional monomer(s)/imprint molecule(s) mole ratio (M/T) inclusively between 0.5/1 and 100/1, more particularly between 1/1 and 30/1 and preferentially between 2/1 and 10/1.

According to a particular embodiment, either of macromolecules obtained from the repetition of units (monomers) of two distinct natures, or of functional monomers as defined previously and of a crosslinking agent.

iii) Optionally, the Crosslinking Agent or Polymer Network

According to a particularly preferred variant of the invention, the polymerization method used for manufacturing the MIPs involves at least one crosslinking agent.

More particularly, the polymerization for obtaining the MIPs of the invention involves a process of "bulk" type. This is a method that is known to those skilled in the art, which consists especially in using polyfunctionalized and preferably difunctionalized crosslinked monomers, such as those derived from acrylate and styrene (see for example: *Encyclopedia of Polymer Science and Technology* mentioned previously, http://onlinelibrary.wiley.com/doi/10.1002/0471440264.pst432/pdf and *Process for preparing MIPs* hereinbelow).

According to another variant, the crosslinking agent used is a sol-gel system as defined previously.

Preferably, the polymerization is performed via a radical route, and particularly in the presence of a polymerization initiator as defined previously.

More particularly, the monomers are of formula (C3) or (C4) below:

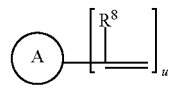

(C3)

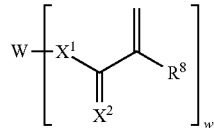

(C4)

in which formulae (C3) and (C4):
A represents an optionally substituted (hetero)aryl group or optionally substituted (hetero)cycloalkyl group, preferably A represents a phenyl;
R$^8$, which may be identical or different, represents a hydrogen atom or an optionally substituted linear or branched (C$_1$-C$_8$)alkyl group, preferably a C$_1$-C$_6$ group, such as methyl;
X$^1$ and X$^2$, which may be identical or different, are as defined previously; preferably X$^1$=O or NH, and X$^2$=O; and more particularly X$^1$=X$^2$=an oxygen atom, or alternatively X$^1$ forms a bond;
W represents: i) either a group A as defined previously, in particular a 5- or 6-membered heteroaryl group such as pyridyl or heterocycloalkyl comprising at least one oxygen atom and being 5- to 8-membered such as tetrahydrofuryl, piperazinyl or hexahydrofuro[3,2-b]furyl, ii) or a group *-A-(CR$^9$R$^{10}$)$_x$-A-* when w is 2, with A as defined previously, R$^9$ and R$^{10}$, which may be identical or different, representing a hydrogen atom or a (C$_1$-C$_6$)alkyl group such as methyl, x represents an integer inclusively between 0 and 10, preferably x=1 and * represents the point of attachment to the groups —X$^1$—C(X$^2$)—C(=CH$_2$)—R$^8$, iii) or a linear or branched polyvalent, preferably divalent or trivalent, saturated or unsaturated, preferably saturated, hydrocarbon-based chain, which is optionally substituted, preferably with a hydroxyl group or with a phenyl group, and comprising from 1 to 20 carbon atoms;
n represents an integer inclusively between 0 and 5; more particularly between 0 and 3, such as n=0 or 1;

u and w represent an integer inclusively between 2 and 10 and more particularly between 2 and 5, such as u=2 and w=3.

Preferably, W represents a divalent $C_1$-$C_6$ or trivalent $C_1$-$C_{10}$ alkyl group.

According to a preferred variant of the invention, the monomers of formulae (C3) and (C4) are chosen from the compounds in the following table, and also the optical and geometrical isomers thereof, tautomers thereof and mineral or organic acid or base salts thereof:

| Name | Abbreviation | Structure |
|---|---|---|
| Styrene/divinylbenzene | (DVB) | 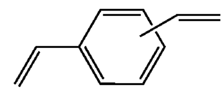 |
| Diisopropylbenzene | (DIB) | 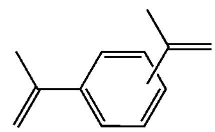 |
| 1,3-Phenylene diacrylamide; 1,4-Phenylene diacrylamide | | 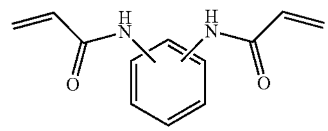 |
| N,N'-1,3-Phenylenebis(2-methyl-2-propenamide); N,N'-1,4-Phenylenebis(2-methyl-2-propenamide) | | 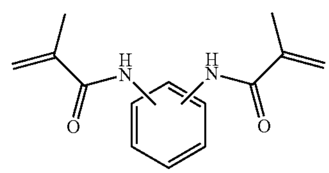 |
| 3,5-Bisacrylamidobenzoic acid with R" identical and equal to H; and 3,5-Bismethylacrylamidobenzoic acid with R" identical and equal to $CH_3$ | | R" = H or $CH_3$ |
| 2,6-bisacryloylamidopyridine with R" identical and equal to H; 2,6-bismethylacryloylamidopyridine with R" identical and equal to $CH_3$ | | R" = H or $CH_3$ |
| 1,4-diacryloylpiperazine with R" identical and equal to H; 1,4-dimethylacryloylpiperazine with R" identical and equal to $CH_3$ | (DAP) | R" = H or $CH_3$ |
| Ethylene glycol dimethacrylate with R" identical and equal to $CH_3$ (EGDMA); Ethylene glycol diacrylate with R" identical and equal to H | (EGDMA) | R" = H or $CH_3$ |

-continued

| Name | Abbreviation | Structure |
|---|---|---|
| Tetramethylene dimethacrylate with R″ identical and equal to $CH_3$; Tetramethylene diacrylate with R″ identical and equal to H | (TDMA) | R″ = H or $CH_3$ |
| Hexamethylene dimethacrylate with R″ identical and equal to $CH_3$ and Hexamethylene diacrylate with R″ identical and equal to H | | R″ = H or $CH_3$ |
| Anhydroerythritol dimethacrylate with R″ identical and equal to $CH_3$ and Anhydroerythritol diacrylate with R″ identical and equal to H | | R″ = H or $CH_3$ |
| 1,4; 3,6-dianhydro-p-sorbitol-2,5-dimethacrylate with R″ identical and equal to $CH_3$; 1,4; 3,6-dianhydro-p-sorbitol-2,5-diacrylate with R″ identical and equal to H | | R″ = H or $CH_3$ |
| Isopropenebis(1,4-phenylene) dimethacrylate with R″ identical and equal to $CH_3$; Isopropenebis(1,4-phenylene) diacrylate with R″ identical and equal to H | | R″ = H or $CH_3$ |
| 2,2-bis(Hydroxymethyl)butanol trimethacrylate with R″ identical and equal to $CH_3$ (TRIM); 2,2-bis(Hydroxymethyl)butanol triacrylate with R″ identical and equal to H | (TRIM) | R″ = H or $CH_3$ |

| Name | Abbreviation | Structure |
|---|---|---|
| Pentaerythritol triacrylate with R" identical and equal to H; Pentaerythritol trimethacrylate with R" identical and equal to CH$_3$ | | R" = H or CH$_3$ |
| Pentaerythritol tetraacrylate with R" identical and equal to H (PETRA); Pentaerythritol tetramethacrylate with R" identical and equal to CH$_3$ | (PETRA) | R" = H or CH$_3$ |
| N,O-bismethacryloylethanolamine with R$_c$ equal to ethylene and R" identical and equal to CH$_3$ | (NOBE) | R$_c$ = (C$_1$-C$_6$)alkylene such as ethylene<br>R" = H or CH$_3$ |
| N,N'-methylenebisacrylamide with R$_c$ = CH$_2$ (MDAA); or N,N-1,2-ethanediylbis(2-methyl-2-propenamide) N,N'-ethylenebisacrylamide with R$_c$ = CH$_2$—CH$_2$; N,N'-butylenebisacrylamide with R$_c$ = CH$_2$—CH$_2$—CH$_2$—CH$_2$; N,N'-hexylenebisacrylamide with R$_c$ = CH$_2$—CH$_2$—CH$_2$—CH$_2$—CH$_2$—CH$_2$ | (MDAA) | R$_c$ = (C$_1$-C$_6$)alkylene<br>R" = H or CH$_3$ |

More particularly, EDMA, TRIM and DVB are used in the polymerization process with the functional monomers to synthesize the MIPs of the invention.

The synthesis of the MIPs according to the invention is preferentially performed via a radical process and more particularly according to the non-covalent approach.

Proportion of Crosslinking Agent:

According to a particular embodiment of the invention, the mass amount of crosslinking agent in the prepolymerization mixture is in excess relative to the mass amount of the functional monomer. Preferentially, the amount of crosslinking agent, as a mass percentage, is greater than or equal to 50%. More preferentially, it is greater than or equal to 80%.

In particular, the ratio of the number of moles of functional monomers to the number of moles of crosslinking agents is less than or equal to $\frac{1}{3}$ (mol/mol) and more particularly the ratio is less than or equal to $\frac{1}{5}$.

According to a particularly appreciated mode of the invention, the amount of functionalized monomer (methacrylic acid MAA)crosslinking agent (ethylene glycol dimethacrylate EGDMA) introduced into the prepolymerization mixture is in a ratio inclusively within the 20/80 mole ratio.

According to an advantageous mode of the invention, the amounts of imprint molecule or template (T), of functionalized monomer (M) and of crosslinking agent (CL) introduced into the prepolymerization mixture are in a ratio inclusively within the mole ratio 1:4:20/T:M:CL and the ratio 1:8:40/T:M:CL. It is understood that (M) the functional monomer may correspond to a mixture of functional monomers, for instance the mixture of AEM and AAm.

Process for Preparing MIPs:

According to a variant in a first stage i) the polymerization initiator(s), which are preferably radical initiator(s) as described previously, ii) the functional monomer(s) as defined previously, iii) optionally the crosslinking agent(s) as defined previously, iv) the porogenic solvent(s) as defined previously, and v) the imprint molecule(s) or templates as defined previously are mixed together. The mixture is preferably placed under an inert atmosphere such as under argon or nitrogen.

In a second stage, the polymerization of the MIP according to the invention is performed in "bulk", i.e. the energy required for the polymerization is provided either thermally, for example via a water bath at 60° C., for example for a few hours (24 hours), or photochemically, especially using as photochemical source a UV lamp particularly at a temperature inclusively between 0° C. and 30° C. and more particularly between 4° C. and 15° C. The hard monolith thus formed, known as the "bulk", is then preferably shaken or is subjected to small impacts and then optionally ground and/or screened.

In a third stage, the extraction of the imprint molecule(s) takes place by (successive) washing and/or by extraction, for example using Soxhlet apparatus or a similar device. The MIP(s) may then be subjected to a purification, for example decantation in a solvent such as acetone, and then to optional screening in order to have particles of a certain size.

The composition of the washing solutions is adapted to the non-specific interactions to be eliminated. Thus, preferentially, the washing solution is an aqueous-organic mixture or an aprotic solvent such as acetonitrile, modified so as to be a polar protic solvent such as a mixture with alcohols, acids, preferably organic acids such as acetic acid, or organic bases such as ammonia and diethylamine. More preferentially, the washing mixture consists predominantly of the porogenic solvent.

According to a particular embodiment of the invention, when the interactions between the functional monomer and the imprint molecule or template are of hydrophobic type, then the washing(s) are performed with any type of solvent, particularly with apolar solvents. When the said interactions are of "dipole-dipole" type, then the preferred washing solvents are polar aprotic solvents such as acetonitrile, dichloromethane, THF or chloroform; when the said interactions are of ionic type, then the preferred washing solvents are strongly polar or even protic such as acids (for example acetic acid) or bases or basifying agents as defined hereinbelow (such as ammonia or diethylamine) in a disassociating solvent such as ethanol.

Thus, as described previously, the polymerization step is advantageously followed by a step of removing the template present in the MIP obtained after the polymerization step.

The removal step may be performed by washing or extraction as described previously.

iv) The Imprint Molecules or Template

The aim of the invention is to provide a polymer of MIP type which takes up molecules that are at the surface of keratin materials in particular the molecules which are secreted by the skin, preferentially odorous molecules or molecules that are the source of unpleasant human body odour such as sweat and sebum.

As seen previously, the "template" is a compound which mimics the molecules that are the cause of the said odours within the MIP in order for the MIP to be able subsequently to take up the odours. The template must therefore be representative of the odorous molecules targeted or of the molecules which are the source of the odours in the sample. The resemblance between the template and the sought molecules must relate equally to their size and shape and to the nature, position and spatial orientation of their functional groups.

These molecules or templates are preferentially chosen from:

a) linear or branched, saturated or unsaturated, and/or optionally substituted $C_2$-$C_{13}$ aliphatic acids such as those of formula (T1) below:

$$R^{11}-C(O)-OH \qquad (T1)$$

in which formula (T1) $R^{11}$ represents i) a linear or branched ($C_1$-$C_{13}$)alkyl group which is optionally substituted, preferably with at least one hydroxyl group, ii) a linear or branched ($C_2$-$C_{13}$)alkenyl group which is optionally substituted, preferably with at least one hydroxyl group; the alkyl or alkenyl group particularly contain between 2 and 13 carbon atoms.

In particular, the odorous molecules are chosen from acetic acid, 2-propenoic acid, propanoic acid, 2-methylpropanoic acid, 2-methylpropenoic acid, 2-butenoic acid, 2-methyl-2-butenoic acid, 3-methyl-2-butenoic acid, butanoic acid, 2-methylbutanoic acid, 3-methylbutanoic acid, 3-hydroxybutanoic acid, 3-hydroxy-3-methylbutanoic acid, 2-pentenoic acid, 2-methyl-2-pentenoic acid, 3-methyl-2-pentenoic acid, pentanoic acid, 2-methylpentanoic acid, 3-methylpentanoic acid, 3-hydroxypentanoic acid, 3-hydroxy-3-methylpentanoic acid, 2-heptenoic acid, 3-methyl-2-hexenoic acid, 3-hydroxy-3-methylhexanoic acid, 3-hydroxy-4-methyloctanoic acid, 3-hydroxyhexanoic acid, 2-methyl-2-heptenoic acid, 3-methyl-2-heptenoic acid, heptanoic acid, 2-methylheptanoic acid, 3-methylheptanoic acid, 3-hydroxyheptanoic acid, 3-hydroxy-3-methylheptanoic acid, 2-octenoic acid, 2-methyl-2-octenoic acid, 3-methyl-2-octenoic acid, octanoic acid, 2-methyloctanoic acid, 3-methyloctanoic acid, 3-hydroxyoctanoic acid, 3-hydroxy-3-methyloctanoic acid, 2-nonenoic acid, 2-methyl-2-nonenoic acid, 3-methyl-2-nonenoic acid, nonanoic acid, 2-methylnonanoic acid, 3-methylnonanoic acid, 3-hydroxynonanoic acid, 3-hydroxy-3-methylnonanoic acid, 2-decenoic acid, 2-methyl-2-decenoic acid, 3-methyl-2-decenoic acid, decanoic acid, 2-methyldecanoic acid, 3-methyldecanoic acid, 3-hydroxydecanoic acid, 3-hydroxy-3-methyldecanoic acid, 10-hydroxydecanoic acid, 2-undecenoic acid, 2-methyl-2-undecenoic acid, 3-methyl-2-undecenoic acid, undecanoic acid, 2-methylundecanoic acid, 3-methylundecanoic acid, 3-hydroxyundecanoic acid, 3-hydroxy-3-methylundecanoic acid, dodecanoic acid, 2-hydroxydodecanoic acid, tridecanoic acid, 2-hydroxydodecanoic acid and tridecanoic acid.

In particular, the acid(s) are branched and/or substituted with at least one hydroxyl group.

More particularly, the odorous molecules are chosen from 2-methylpropanoic acid, 3-methyl-2-hexenoic acid, 3-hydroxy-3-methylhexanoic acid, 3-hydroxy-4-methyloctanoic acid, 3-hydroxyhexanoic acid and 3-hydroxyoctanoic acid.

b) Sulfanylalkanols (or mercaptoalkanols) such as those of formula (T2) below:

$$HS-R^{12}-OH \qquad (T2)$$

in which formula (T2) $R^{12}$ represents a linear or branched ($C_1$-$C_{10}$) and preferably ($C_1$-$C_6$) alkylene group.

In particular, the odorous molecules are chosen from 3-methyl-3-sulfanylhexan-1-ol, 3-sulfanylhexan-1-ol, 2-methyl-3-sulfanylbutan-1-ol, 3-sulfanylpentan-1-ol, 3-sulfanylbutan-1-ol, 3-methyl-3-sulfanylpentan-1-ol and 3-methyl-3-sulfanylbutan-1-ol.

c) Steroids such as those of formula (T3) below:

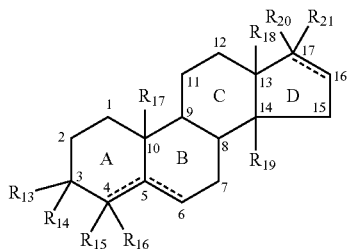

and also optical isomers thereof, cosmetic organic or mineral acid or base salts thereof, and solvates such as hydrates,
in which formula (T3):
$R_{13}$ and $R_{14}$, which may be identical or different, represent a hydrogen atom or a hydroxyl group, or alternatively $R_{13}$ and $R_{14}$ form, together with the carbon atom that bears them, an oxo group;
$R_{15}$ and $R_{16}$, which may be identical or different, represent a hydrogen atom, a linear or branched $(C_1$-$C_8)$alkyl group, such as methyl, or a hydroxyl group, or alternatively
$R_{15}$ and $R_{16}$ form, together with the carbon atom that bears them, an oxo group, in which case the bond between carbon atoms 4 and 5 is a single bond;
= represents a single or a double bond, it being understood that when one of the two bonds between the two carbon atoms 4 and 5 or 5 and 6 is a double bond, then the other bond is a single bond;
$R_{17}$, $R_{18}$ and $R_{19}$, which may be identical or different, represent a hydrogen atom or a linear or branched $(C_1$-$C_8)$alkyl group, such as methyl;
$R_{20}$ and $R_{21}$, which may be identical or different, represent a hydrogen atom, a linear or branched $(C_1$-$C_8)$alkyl group, such as methyl, a hydroxyl group, a group —$C(X^1)$—$X^2$—$R_{22}$, —$X^2$—$C(X^1)$—$R_{22}$, —$C(X^1)$—$R_{22}$, with $X^1$ and $X^2$ being as defined previously, preferably represents an oxygen atom, $R_{22}$ representing a hydrogen atom or a $(C_1$-$C_6)$alkyl group optionally substituted with a hydroxyl group, or alternatively $R_{20}$ and $R_{21}$ form, together with the carbon atom that bears them, an oxo group, in which case the bond between carbon atoms 16 and 17 is a single bond.
Mention may be made in particular of steroids chosen from androst-16-ene steroids, especially 5α-androst-16-en-3-one and 5α-androst-16-en-3α-ol, androst-2-en-17-one, androsta-4,16-dien-3-one, androsta-5,16-dien-3-ol, androst-4-en-3,17-dione, androstan-3-one, DHEA (dehydroepiandrosterone), testosterone, DHT (dehydrotestosterone) and 3-hydroxy-5-androstan-17-one.

d) Molecules chosen from amino acids such as those of formula (T4) below:

in which formula (T4):
$R_{23}$ and $R_{24}$, which may be identical or different, represent a —$C(X^1)$—$X^2$—$R_{25}$, —$X^2$—$C(X^1)$—$R_{25}$, —$C(X^1)$—$R_{25}$, with $X^1$ and $X^2$ as defined previously, preferably $X^1$ represents an oxygen atom and $X^2$ represents an NH group; $R_{25}$ representing a hydrogen atom, a linear or branched $(C_1$-$C_8)$alkyl or linear or branched $(C_2$-$C_8)$alkenyl group, such as methyl, optionally substituted with a hydroxyl group;
ALK represents a linear or branched $(C_1$-$C_8)$alkylene group, optionally substituted with a group —$C(X^1)$—$X^2$—$R_{25}$, or —$X^2$—$C(X^1)$—$R_{25}$, with $R_{25}$, $X^1$ and $X^2$ as defined previously, preferably ALK is a linear $C_2$-$C_4$ group such as a linear $C_3$ group, substituted with a carboxyl group.

In particular, mention may be made of the conjugated product of glutamine with 3-methyl-2-hexenoic acid and the conjugated product of glutamine with 3-hydroxy-3-methylhexanoic acid, N2-[3-methylhex-2-enoyl]glutamine, N2-[3-methyl-3-hydroxyhexanoyl]glutamine, N2-acetylglutamine, N2-[prop-2-enoyl]glutamine, N2-[2-methylprop-2-enoyl]glutamine, N2-propanoylglutamine, N2-[2-methylpropanoyl]glutamine, N2-[but-2-enoyl]glutamine, N2-[2-methylbut-2-enoyl]glutamine, N2-butanoylglutamine, N2-[2-methylbutanoyl]glutamine, N2-[3-methylbutanoyl]glutamine, N2-[3-hydroxybutanoyl]glutamine, N2-[3-hydroxy-3-methylbutanoyl]glutamine, N2-[pent-2-enoyl]glutamine, N2-[2-methylpent-2-enoyl]glutamine, N2-pentanoylglutamine, N2-[2-methylpentanoyl]glutamine, N2-[3-methylpentanoyl]glutamine, N2-[3-hydroxypentanoyl]glutamine, N2-[3-hydroxy-3-methylpentanoyl]glutamine, N2-[hex-2-enoyl]glutamine, N2-[2-methylhex-2-enoyl]glutamine, N2-hexanoylglutamine, N2-[2-methylhexanoyl]glutamine, N2-[3-methylhexanoyl]glutamine, N2-[3-hydroxyhexanoyl]glutamine, N2-[hept-2-enoyl]glutamine, N2-[2-methylhept-2-enoyl]glutamine, N2-heptanoylglutamine, N2-[2-methylheptanoyl]glutamine, N2-[3-methylheptanoyl]glutamine, N2-[3-hydroxyheptanoyl]glutamine, N2-[3-hydroxy-3-methylheptanoyl]glutamine, N2-[oct-2-enoyl]glutamine, N2-[2-methyloct-2-enoyl]glutamine, N2-octanoylglutamine, N2-[2-methyloctanoyl]glutamine, N2-[3-methyloctanoyl]glutamine, N2-[3-hydroxyoctanoyl]glutamine, N2-[3-hydroxy-3-methyloctanoyl]glutamine, N2-[non-2-enoyl]glutamine, N2-[2-methylnon-2-enoyl]glutamine, N2-nonanoylglutamine, N2-[2-methylnonanoyl]glutamine, N2-[3-methylnonanoyl]glutamine, N2-[3-hydroxynonanoyl]glutamine, N2-[3-hydroxy-3-methylnonanoyl]glutamine, N2-[dec-2-enoyl]glutamine, N2-[2-methyldec-2-enoyl]glutamine, N2-decanoylglutamine, N2-[2-methyldecanoyl]glutamine, N2-[3-methyldecanoyl]glutamine, N2-[3-hydroxydecanoyl]glutamine, N2-[3-hydroxy-3-methyldecanoyl]glutamine, N2-[undec-2-enoyl]glutamine, N2-[2-methylundec-2-enoyl]glutamine, N2-undecanoylglutamine, N2-[2-methylundecanoyl]glutamine, N2-[3-methylundecanoyl]glutamine, N2-[3-hydroxyundecanoyl]glutamine, N2-[3-hydroxy-3-methylundecanoyl]glutamine, N2-[dodec-2-enoyl]glutamine, N2-[2-methyldodec-2-enoyl]glutamine, N2-dodecanoylglutamine, N2-[2-methyldodecanoyl]glutamine, N2-[3-methyldodecanoyl]glutamine, N2-[3-hydroxydodecanoyl]glutamine, N2-[3-hydroxy-3-methyldodecanoyl]glutamine and Nα-hexanoylglutamine.

In particular, mention may be made of the conjugated product of glutamic acid with 3-methyl-2-hexenoic acid and the conjugated product of glutamic acid with 3-hydroxy-3-methylhexanoic acid, N2-[3-methylhex-2-enoyl]glutamic acid, N2-[3-methyl-3-hydroxyhexanoyl]glutamic acid, N2-acetylglutamic acid, N2-[prop-2-enoyl]glutamic acid, N2-[2-methylprop-2-enoyl]glutamic acid, N2-propanoylglutamic acid, N2-[2-methylpropanoyl]glutamic acid, N2-[but-2-enoyl]glutamic acid, N2-[2-methylbut-2-enoyl]glutamic acid, N2-butanoylglutamic acid, N2-[2- methylbutanoyl]glutamic acid, N2-[3-methylbutanoyl] glutamic acid, N2-[3-hydroxybutanoyl]glutamic acid, N2-[3-hydroxy-3-methylbutanoyl]glutamic acid, N2-[pent-2-enoyl]glutamic acid, N2-[2-methylpent-2-enoyl]glutamic acid, N2-pentanoylglutamic acid, N2-[2-methylpentanoyl] glutamic acid, N2-[3-methylpentanoyl]glutamic acid, N2-[3-hydroxypentanoyl]glutamic acid, N2-[3-hydroxy-3-methylpentanoyl]glutamic acid, N2-[hex-2-enoyl]glutamic acid, N2-[2-methylhex-2-enoyl]glutamic acid, N2-hexanoylglutamic acid, N2-[2-methylhexanoyl]glutamic acid, N2-[3-methylhexanoyl]glutamic acid, N2-[3-hydroxyhexanoyl]glutamic acid, N2-[hept-2-enoyl]glutamic acid, N2-[2-methylhept-2-enoyl]glutamic acid, N2-heptanoylglutamic acid, N2-[2-methylheptanoyl]glutamic acid, N2-[3-methylheptanoyl]glutamic acid, N2-[3-hydroxyheptanoyl]glutamic acid, N2-[3-hydroxy-3-methylheptanoyl] glutamic acid, N2-[oct-2-enoyl]glutamic acid, N2-[2-methyloct-2-enoyl]glutamic acid, N2-octanoylglutamic acid, N2-[2-methyloctanoyl]glutamic acid, N2-[3-methyloctanoyl] glutamic acid, N2-[3-hydroxyoctanoyl]glutamic acid, N2-[3-hydroxy-3-methyloctanoyl]glutamic acid, N2-[non-2-enoyl]glutamic acid, N2-[2-methylnon-2-enoyl]glutamic acid, N2-nonanoylglutamic acid, N2-[2-methylnonanoyl] glutamic acid, N2-[3-methylnonanoyl]glutamic acid, N2-[3-hydroxynonanoyl]glutamic acid, N2-[3-hydroxy-3-methylnonanoyl]glutamic acid, N2-[dec-2-enoyl]glutamic acid, N2-[2-methyldec-2-enoyl]glutamic acid, N2-decanoylglutamic acid, N2-[2-methyldecanoyl]glutamic acid, N2-[3-methyldecanoyl]glutamic acid, N2-[3-hydroxydecanoyl] glutamic acid, N2-[3-hydroxy-3-methyldecanoyl]glutamic acid, N2-[undec-2-enoyl]glutamic acid, N2-[2-methylundec-2-enoyl]glutamic acid, N2-undecanoylglutamic acid, N2-[2-methylundecanoyl]glutamic acid, N2-[3-methylundecanoyl]glutamic acid, N2-[3-hydroxyundecanoyl]glutamic acid, N2-[3-hydroxy-3-methylundecanoyl]glutamic acid, N2-[dodec-2-enoyl]glutamic acid, N2-[2-methyldodec-2-enoyl]glutamic acid, N2-dodecanoylglutamic acid, N2-[2-methyldodecanoyl]glutamic acid, N2-[3-methyldodecanoyl]glutamic acid, N2-[3-hydroxydodecanoyl]glutamic acid, N2-[3-hydroxy-3-methyldodecanoyl]glutamic acid and Nα-hexanoylglutamic acid.

e) Acid esters such as the acid esters of formula (T1) as defined previously, preferentially the esters of formula (T'1) below:

$$R^{11}\text{—}C(O)\text{—}OR'^{11} \tag{T'1}$$

in which formula (T'1):
$R^{11}$ is as defined previously; and
$R'^{11}$ represents i) a linear or branched ($C_1$-$C_{20}$)alkyl group which is optionally substituted, preferably with at least one hydroxyl group, ii) a linear or branched ($C_2$-$C_{20}$)alkenyl group which is optionally substituted, preferably with at least one hydroxyl group; the alkyl or alkenyl group particularly contain between 2 and 14 carbon atoms, and more particularly $R'^{11}$ represents a linear or branched ($C_1$-$C_6$) alkyl group such as methyl.

In particular, the methyl esters of the following acids are chosen: acetic acid, 2-propenoic acid, propanoic acid, 2-methylpropanoic acid, 2-methylpropenoic acid, 2-butenoic acid, 2-methyl-2-butenoic acid, 3-methyl-2-butenoic acid, butanoic acid, 2-methylbutanoic acid, 3-methylbutanoic acid, 3-hydroxybutanoic acid, 3-hydroxy-3-methylbutanoic acid, 2-pentenoic acid, 2-methyl-2-pentenoic acid, 3-methyl-2-pentenoic acid, pentanoic acid, 2-methylpentanoic acid, 3-methylpentanoic acid, 3-hydroxypentanoic acid, 3-hydroxy-3-methylpentanoic acid, 3-methyl-2-hexenoic acid, 3-hydroxy-3-methylhexanoic acid, 3-hydroxy-4-methyloctanoic acid, 3-hydroxyhexanoic acid, 2-heptenoic acid, 2-methyl-2-heptenoic acid, 3-methyl-2-heptenoic acid, heptanoic acid, 2-methylheptanoic acid, 3-methylheptanoic acid, 3-hydroxyheptanoic acid, 3-hydroxy-3-methylheptanoic acid, 2-octenoic acid, 2-methyl-2-octenoic acid, 3-methyl-2-octenoic acid, octanoic acid, 2-methyloctanoic acid, 3-methyloctanoic acid, 3-hydroxyoctanoic acid, 3-hydroxy-3-methyloctanoic acid, 2-nonenoic acid, 2-methyl-2-nonenoic acid, 3-methyl-2-nonenoic acid, nonanoic acid, 2-methylnonanoic acid, 3-methylnonanoic acid, 3-hydroxynonanoic acid, 3-hydroxy-3-methylnonanoic acid, 2-decenoic acid, 2-methyl-2-decenoic acid, 3-methyl-2-decenoic acid, decanoic acid, 2-methyldecanoic acid, 3-methyldecanoic acid, 3-hydroxydecanoic acid, 3-hydroxy-3-methyldecanoic acid, 10-hydroxydecanoic acid, 2-undecenoic acid, 2-methyl-2-undecenoic acid, 3-methyl-2-undecenoic acid, undecanoic acid, 2-methylundecanoic acid, 3-methylundecanoic acid, 3-hydroxyundecanoic acid, 3-hydroxy-3-methylundecanoic acid, dodecanoic acid, 2-hydroxydodecanoic acid, tridecanoic acid, 2-hydroxydodecanoic acid or tridecanoic acid.

In particular, mention may be made of the odorous compounds of formula (T'1) chosen from the methyl ester of 3-hydroxy-3-methylhexanoic acid, the methyl ester of 3-hydroxy-4-methyloctanoic acid, the methyl ester of (E)-3-methyl-2-hexenoic acid, the methyl ester of 3-hydroxyhexanoic acid and the methyl ester of 3-hydroxyoctanoic acid.

More particularly, the methyl esters of the following acids: 2-methylpropanoic acid, 3-methyl-2-hexenoic acid, 3-hydroxy-3-methylhexanoic acid, 3-hydroxy-4-methyloctanoic acid, 3-hydroxyhexanoic acid and 3-hydroxyoctanoic acid.

f) The conjugated products of 3-methyl-3-sulfanylhexan-1-ol in particular of formula (T'4) below:

$$R_{25}\text{—}X^2\text{—}C(X^1)\text{-}ALK\text{-}X'^2\text{—}C(X'^1)\text{—}CH(X''^2H)\text{-}ALK'\text{-}S\text{—}R'_{25} \tag{T'4}$$

in which formula (T'4):
$R_{25}$ and $R'_{25}$, which may be identical or different, represent a hydrogen atom, a linear or branched ($C_1$-$C_8$)alkyl or linear or branched ($C_2$-$C_8$)alkenyl group, such as methyl, optionally substituted with a hydroxyl group; preferably, $R_{25}$ represents a hydrogen atom and $R'_{25}$ represents a ($C_1$-$C_6$)alkyl group optionally substituted with a hydroxyl group;
ALK and ALK', which may be identical or different, represent a linear or branched ($C_1$-$C_8$)alkylene group optionally substituted with a group —$X^2$—$R_{25}$, with $R_{25}$;
$X^1$ and $X^2$, which may be identical or different, are as defined previously, preferably $X^1$=$X^2$=O;
$X'^1$ and $X'^2$, and $X''^2$, which may be identical or different, are as defined for $X^1$ and $X^2$ respectively, preferably $X'^2$=$X''^2$=NH and/or $X'^1$=O.

In particular, the odorous compounds are chosen from the following compounds: S-(1-hydroxy-3-methylhexan-3-yl) cysteinylglycine, S-(1-hydroxy-2-methylhexan-3-yl)cysteinylglycine, S-(1-hydroxy-2-methylbutan-3-yl)cysteinylglycine, S-(1-hydroxypentan-3-yl)cysteinylglycine, S-(1-hydroxybutan-3-yl)cysteinylglycine, S-(1-hydroxy-3-methylpentan-3-yl)cysteinylglycine, S-(1-hydroxy-3-methylbutan-3-yl)cysteinylglycine, S-(1-hydroxyhexan-3-yl)cysteinylglycine and S-(1-hydroxy-2-methylhexan-3-yl) cysteinylglycine, and also the enantiomers and racemic mixtures thereof.

g) Sulfo-conjugated steroids, in particular the sulfate derivatives of formula (T3) as defined previously, which comprise at least one sulfate function.

In particular, the odorous compounds are chosen from the sulfates derived from dehydroepiandrosterone (DH EA), androsterone and testosterone, 5α-androst-16-en-3α-sulfate, androsta-5,16-dien-3β-sulfate, dehydroepiandrosterone sulfate, testosterone sulfate, 5α-dehydrotestosterone sulfate and 5α-androstan-17-on-3α-sulfate.

Preferably, the imprint molecule(s) are of formula (T4) and in particular the conjugated product of glutamine such as Nα-hexanoylglutamine.

v) The Porogenic Solvent

The MIPs are prepared from porogenic solvent, the polarity of which preferably i) makes it possible to dissolve the imprint molecule and/or ii) is suited to the interaction of the said imprint molecule with the functional monomers.

The term "porogenic" solvent means a solvent that is capable of creating a porous network capable of conveying the templates or odorous molecules or the molecules that are the source of the unpleasant odour to the imprints in the formed polymer.

According to a particular embodiment of the invention, the volume of porogenic solvent used for the preparation of a "bulk" polymer as defined previously is calculated by means of the following relationship $\underline{n}=V_{porogenic\ solvent}/(V_{porogenic\ solvent}+V_{functional\ monomer})$, with $\underline{n}$ inclusively between 0.2 and 0.9, more particularly between 0.3 and 0.8 and preferentially between 0.5 and 0.6.

According to a preferred mode of the invention, when hydrogen bonds or ionic interactions or coordination bonds with transition metals are involved, the porogenic solvents in the process for synthesizing the MIP(s) of the invention are solvents of weak hydrogen-bond donating or accepting nature, and which are sparingly polar, of the type such as benzene, toluene, chloroform or dichloromethane.

According to a preferred mode, when the dissolution of the imprint molecule in the prepolymerization mixture demands it, the porogenic solvent is a polar protic solvent such as $C_1$-$C_8$ alcohols, for instance ethanol.

According to another preferred embodiment, the porogenic solvent is a polar aprotic solvent such as acetonitrile, tetrahydrofuran (THF), dialkylformamides (dimethylformamide, diethylformamide), N-methyl-2-pyrrolidinone (NMP), N-ethyl-2-pyrrolidinone (NEP), N,N'-dimethylpropyleneurea (DMPU) and dimethyl sulfoxide (DMSO).

According to a particularly advantageous mode, the composition of the invention comprising the MIP(s) also comprises at least one cosmetic porogenic solvent used during the synthesis of the said MIP(s) with the imprint molecule(s).

Advantageously, the porogenic solvent may be supplemented with a modifier of hydrogen-bond donor or acceptor nature, which is acidic, rather organic acids, in particular ($C_1$-$C_8$)carboxylic acids such as acetic acid; and/or which is basic, rather organic bases of the (di)($C_1$-$C_8$)alkylamine type such as diethylamine.

Preferentially, the porogenic solvent used in the invention for preparing the MIPs is a solvent chosen from (a) polar protic solvents such as $C_1$-$C_8$ alcohols, for instance ethanol, and acetonitrile.

Characterization of the MIP

The characterization of the MIP consists in demonstrating the formation of imprints and in evaluating their number and their affinity for the targeted molecule. These results may be complemented by a study of the morphology of the material (size and shape of the particles, porosity and specific surface area). These methods are known to those skilled in the art (see for example point 1.7, p 49 of the June 2010 doctoral thesis by R. Walsh, Development and characterization of MIP http://repository.wit.ie/1619/1/Development_and_characterisation_of_molecularly_imprinted_suspension_polymers.pdf)

Cosmetic Compositions:

The cosmetic composition according to the invention is a composition which is in a physiologically acceptable medium, which is preferentially a dermatologically acceptable medium, i.e. a medium which has no odour or unpleasant aspect, and which is perfectly compatible with the topical administration route.

In the present case, where the composition is intended for topical administration, that is to say for administration by application at the surface of the keratin material under consideration, such a medium is considered in particular to be physiologically acceptable when it does not cause stinging, tightness or redness unacceptable to the user.

A physiologically acceptable medium is preferentially a cosmetically or dermatologically acceptable medium, that is to say a medium which is devoid of unpleasant odour or appearance and which is entirely compatible with the topical administration route.

In the present case, where the composition is intended for topical administration, that is to say for administration by application at the surface of the keratin material under consideration, such a medium is considered in particular to be physiologically acceptable when it does not cause stinging, tightness or redness unacceptable to the user.

The cosmetic composition according to the invention may be water or a mixture of water and of one or more organic solvents or a mixture of organic solvents.

The term "organic solvent" means an organic substance that is capable of dissolving or dispersing another substance without chemically modifying it.

The deodorant cosmetic composition may also comprise, besides the MIPs in accordance with the invention, at least one additional deodorant active agent and/or at least one antiperspirant active agent as defined below.

Deodorant Active Agents

According to a particular embodiment of the invention, the composition according to the invention contains one or more deodorant active agents, for instance:

bacteriostatic agents or other bactericidal agents, such as 2,4,4'-trichloro-2'-hydroxydiphenyl ether (triclosan), 2,4-dichloro-2'-hydroxydiphenyl ether, 3',4',5'-trichlorosalicylanilide, 1-(3',4'-dichlorophenyl)-3-(4'-chlorophenyl)urea (triclocarban) or 3,7,11-trimethyldodeca-2,5,10-trienol (farnesol); quaternary ammonium salts, such as cetyltrimethylammonium salts or cetylpyridinium salts; chlorhexidine and its salts; diglyceryl monocaprate, diglyceryl monolaurate, glyceryl monolaurate; polyhexamethylene biguanide salts;

zinc salts;

odour absorbers such as zeolites, cyclodextrins, metal oxide silicates such as those described in patent application US 2005/063 928; metal oxide particles modified with a transition metal, as described in patent applications US 2005/084 464 and US 2005/084 474, aluminosilicates such as those described in patent application EP 1 658 863, chitosan-based particles such as those described in patent U.S. Pat. No. 6,916,465;

substances which block the enzymatic reactions responsible for the formation of odorous compounds, such as arylsulfatase, 5-lipoxygenase, aminocylase or (3-glucuronidase inhibitors;

and mixtures thereof.

The deodorant active agents can be present in the composition according to the invention in a proportion of from 0.01% to 10% by weight and preferably in a proportion of from 0.1% to 5% by weight, with respect to the total weight of the composition.

Antiperspirant Active Agents

The antiperspirant active agents are preferably chosen from aluminium and/or zirconium salts; complexes of zirconium hydroxychloride and of aluminium hydroxychloride with an amino acid, such as those described in patent U.S. Pat. No. 3,792,068, commonly known as "ZAG" complexes. Such complexes are generally known under the name ZAG (when the amino acid is glycine). Mention may be made, among these products, of aluminium zirconium octachlorohydrex GLY, aluminium zirconium pentachlorohydrex GLY, aluminium zirconium tetrachlorohydrate GLY and aluminium zirconium trichlorohydrate GLY.

Use will more particularly be made of aluminium chlorohydrate in the activated or non-activated form.

The antiperspirant active agents can be present in the composition according to the invention in a proportion of from 0.001% to 30% by weight and preferably in a proportion of from 0.5% to 25% by weight, with respect to the total weight of the composition.

Galenical Forms

The composition according to the invention can be provided in any formulation form conventionally used for a topical application and in particular in the form of aqueous gels or of aqueous or aqueous/alcoholic solutions. They can also, by addition of a fatty or oily phase, be provided in the form of dispersions of the lotion type, of emulsions with a liquid or semi-liquid consistency of the milk type, obtained by dispersion of a fatty phase in an aqueous phase (O/W) or vice versa (W/O), or of suspensions or emulsions with a soft, semi-solid or solid consistency of the cream or gel type, or alternatively of multiple emulsions (W/O/W or O/W/O), of microemulsions, of vesicular dispersions of ionic and/or nonionic type, or of wax/aqueous phase dispersions. These compositions are prepared according to the usual methods.

The compositions according to the invention may especially be conditioned in pressurized form in an aerosol device or in a pump-dispenser bottle; conditioned in a device equipped with a perforated wall, especially a grate; conditioned in a device equipped with a ball applicator ("roll-on"); conditioned in the form of wands (sticks) or in the form of a loose or compacted powder. In this regard, they comprise the ingredients generally used in products of this type, which are well known to a person skilled in the art.

According to another specific form of the invention, the compositions according to the invention can be anhydrous.

The term "anhydrous composition" means a composition containing less than 2% by weight of water, or even less than 0.5% of water, relative to the total weight of the composition, and especially free of water, the water not being added during the preparation of the composition but corresponding to the residual water provided by the mixed ingredients.

According to another specific form of the invention, the compositions according to the invention can be solid, in particular in the wand or stick form.

The term "solid composition" is intended to denote a composition for which the maximum force measured by texturometry during the penetration of a probe into the sample of formula is at least equal to 0.25 newtons, in particular at least equal to 0.30 newtons and especially at least equal to 0.35 newtons, assessed under precise measuring conditions as follows.

The formulae are poured hot into jars with a diameter of 4 cm and a depth of 3 cm. Cooling is carried out at ambient temperature. The hardness of the formulae produced is measured after an interval of 24 hours. The jars containing the samples are characterized in texturometry using a texture analyzer, such as that sold by Rheo, TA-XT2, according to the following protocol: a probe of stainless-steel ball type with a diameter of 5 mm is brought into contact with the sample at a rate of 1 mm/s. The measurement system detects the interface with the sample, with a detection threshold equal to 0.005 newton. The probe sinks 0.3 mm into the sample, at a rate of 0.1 mm/s. The measuring device records the change in the force measured in compression over time, during the penetration phase. The hardness of the sample corresponds to the mean of the maximum values of the force detected during the penetration, over at least three measurements.

Aqueous Phase

The compositions according to the invention intended for cosmetic use can comprise at least one aqueous phase. They are especially formulated as aqueous lotions or as water-in-oil or oil-in-water emulsions or as multiple emulsions (oil-in-water-in-oil or water-in-oil-in-water triple emulsions (such emulsions are known and described, for example, by C. Fox in "Cosmetics and Toiletries"—November 1986—Vol. 101—pages 101-112)).

The aqueous phase of the said compositions contains water and generally other water-soluble or water-miscible solvents. The water-soluble or water-miscible solvents comprise monoalcohols with a short chain, for example of $C_1$-$C_4$, such as ethanol or isopropanol; diols or polyols, for instance ethylene glycol, 1,2-propylene glycol, 1,3-butylene glycol, hexylene glycol, diethylene glycol, dipropylene glycol, 2-ethoxyethanol, diethylene glycol monomethyl ether, triethylene glycol monomethyl ether and sorbitol. Propylene glycol, glycerol and 1,3-propanediol will be used more particularly.

The composition according to the invention preferably has a pH ranging from 3 to 9, according to the support chosen.

According to a particular mode of the invention, the pH of the composition(s) is neutral or even slightly acidic. Preferably, the pH of the composition is between 6 and 7.

The pH of these compositions may be adjusted to the desired value by means of acidifying or basifying agents usually used in cosmetics, or alternatively using standard buffer systems.

The term "basifying agent" or "base" means an agent for increasing the pH of the composition in which it is present. The basifying agent is a Brønsted, Lowry or Lewis base. It may be mineral or organic. In particular, the said agent is chosen from a) aqueous ammonia, b) (bi)carbonate, c) alkanolamines such as monoethanolamine, diethanolamine, triethanolamine and derivatives thereof, d) oxyethylenated and/or oxypropylenated ethylenediamines, e) organic amines, f) mineral or organic hydroxides, g) alkali metal silicates such as sodium metasilicates, h) amino acids, preferably basic amino acids such as arginine, lysine, ornithine, citrulline and histidine, and i) the compounds of formula (I) below:

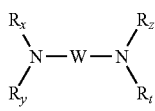 (I)

in which formula (I):
- W is a divalent $C_1$-$C_6$ alkylene radical optionally substituted with one or more hydroxyl groups or a $C_1$-$C_6$ alkyl radical, and/or optionally interrupted with one or more heteroatoms such as oxygen or $NR_u$;
- $R_x$, $R_y$, $R_z$, $R_t$ and $R_u$, which may be identical or different, represent a hydrogen atom or a $C_1$-$C_6$ alkyl, $C_1$-$C_6$ hydroxyalkyl or $C_1$-$C_6$ aminoalkyl radical.

Examples of amines of formula (I) that may be mentioned include 1,3-diaminopropane, 1,3-diamino-2-propanol, spermine and spermidine.

The term "alkanolamine" means an organic amine comprising a primary, secondary or tertiary amine function, and one or more linear or branched $C_1$-$C_8$ alkyl groups bearing one or more hydroxyl radicals.

Among the mineral or organic hydroxides, mention may be made of those chosen from a) hydroxides of an alkali metal, b) hydroxides of an alkaline-earth metal, for instance sodium hydroxide or potassium hydroxide, c) hydroxides of a transition metal, d) hydroxides of lanthanides or actinides, quaternary ammonium hydroxides and guanidinium hydroxide. The mineral or organic hydroxides a) and b) are preferred.

Among the acidifying agents for the compositions used in the invention, examples that may be mentioned include inorganic or organic acids, for instance hydrochloric acid, orthophosphoric acid, sulfuric acid, carboxylic acids, for instance acetic acid, tartaric acid, citric acid or lactic acid, or sulfonic acids.

The basifying agents and the acidifying agents as defined previously preferably represent from 0.001% to 20% by weight relative to the weight of the composition containing them and more particularly from 0.005% to 8% by weight of the composition.

Excipients:

The composition may also comprise one or more additional ingredients. It is understood that the amount of these ingredients may be adjusted by a person skilled in the art so as not to harm the desired effect in the context of the present invention. Among these ingredients, mention may be made of emulsifiers, fatty phases, oils, structuring agents, waxes, pasty compounds other than waxes, gelling agents (organic lipophilic gelling agents), thickeners, suspension agents, propellants and additives. Among these, mention may be made more particularly of:

Oil-in-Water Emulsifiers

The composition according to the invention may comprise at least one emulsifier. As emulsifiers that may be used in the oil-in-water emulsions or oil-in-water-in-oil triple emulsions, examples that may be mentioned include nonionic emulsifiers such as oxyalkylenated fatty acid esters of glycerol; oxyalkylenated fatty alkyl ethers; sugar esters such as sucrose stearate; and mixtures thereof.

Water-in-Oil Emulsifiers

Among the emulsifiers that may be used in the water-in-oil emulsions or water-in-oil-in-water-in-oil triple emulsions, examples that may be mentioned include alkyl dimethicone copolyols.

Mention will also be made, among the water-in-oil emulsifiers, of nonionic emulsifiers derived from fatty acids and polyols, alkyl polyglycosides (APGs), sugar esters and their mixtures.

The total amount of emulsifiers in the composition will preferably be, in the composition according to the invention, at active material contents ranging from 1% to 8% by weight and more particularly from 2% to 6% by weight, with respect to the total weight of the composition.

Fatty Phase

The compositions according to the invention can comprise at least one water-immiscible organic liquid phase, known as fatty phase. This phase generally comprises one or more hydrophobic compounds which render the said phase water-immiscible. The said phase is liquid (in the absence of structuring agent) at room temperature (20-25° C.). Preferentially, the water-immiscible organic-liquid organic phase in accordance with the invention generally comprises at least one volatile oil and/or non-volatile oil and optionally at least one structuring agent.

Oil(s)

The term "oil" means a fatty substance that is liquid at room temperature (25° C.) and atmospheric pressure (760 mmHg, i.e. $10^5$ Pa). The oil may be volatile or non-volatile.

For the purposes of the invention, the term "volatile oil" means an oil that is capable of evaporating on contact with the skin or the keratin fibre in less than one hour, at room temperature and atmospheric pressure. The volatile oils of the invention are volatile cosmetic oils which are liquid at ambient temperature and which have a non-zero vapour pressure, at ambient temperature and atmospheric pressure, ranging from 0.13 Pa to 40 000 Pa ($10^{-3}$ to 300 mmHg), in particular ranging from 1.3 Pa to 13 000 Pa (0.01 to 100 mmHg) and more particularly ranging from 1.3 Pa to 1300 Pa (0.01 to 10 mmHg).

The term "non-volatile oil" means an oil that remains on the skin or the keratin fibre at room temperature and atmospheric pressure for at least several hours, and that especially has a vapour pressure of less than $10^{-3}$ mmHg (0.13 Pa).

The oil can be chosen from any physiologically acceptable oil and in particular cosmetically acceptable oils, in particular mineral, animal, vegetable or synthetic oils; in particular volatile or non-volatile hydrocarbon-based oils and/or silicone oils and/or fluoro oils, and mixtures thereof.

More precisely, the term "hydrocarbon-based oil" means an oil mainly comprising carbon and hydrogen atoms and optionally one or more functions chosen from hydroxyl, ester, ether and carboxylic functions. Generally, the oil exhibits a viscosity of 0.5 to 100 000 mPa·s, preferably of 50 to 50 000 mPa·s and more preferably of 100 to 30 000 mPa·s.

Structuring Agent(s)

The compositions according to the invention comprising a fatty phase can additionally comprise at least one structuring agent for the said fatty phase, which can preferably be chosen from waxes, pasty compounds, inorganic or organic lipophilic gelling agents, and their mixtures.

Wax(es)

The wax is generally a lipophilic compound which is solid at ambient temperature (25° C.), which exhibits a reversible solid/liquid change in state and which has a melting point of greater than or equal to 30° C. which can range up to 200° C. and in particular up to 120° C.

In particular, the waxes suitable for the invention can exhibit a melting point of greater than or equal to 45° C. and in particular of greater than or equal to 55° C.

The composition according to the invention will preferably comprise a content of wax(es) ranging from 3% to 20% by weight relative to the total weight of the composition, in particular from 5% to 15% and more particularly from 6% to 15%.

According to one particular form of the invention, in the context of anhydrous solid compositions in stick form, use will be made of polyethylene microwaxes in the form of crystallites with an aspect ratio at least equal to 2, and with a melting point ranging from 70 to 110° C. and preferably from 70 to 100° C., so as to reduce or even eliminate the presence of strata in the solid composition. These crystallites in needle form and in particular their dimensions can be characterized visually according to the following method.

Pasty Compound(s)

For the purposes of the present invention, the term "pasty compound" means a lipophilic fatty compound that undergoes a reversible solid/liquid change of state, having in the solid state an anisotropic crystal organization, and comprising, at a temperature of 23° C., a liquid fraction and a solid fraction.

Organic Lipophilic Gelling Agents

The polymeric organic lipophilic gelling agents are, for example, partially or totally crosslinked elastomeric organopolysiloxanes, of three-dimensional structure, such as those sold under the names.

Additives

The cosmetic compositions according to the invention may also comprise cosmetic adjuvants chosen from softeners, antioxidants, opacifiers, stabilizers, moisturizers, vitamins, bactericides, preserving agents, polymers, fragrances, organic powders or any other ingredient usually used in cosmetics for this type of application.

Thickeners and Suspending Agents

The compositions according to the invention may also comprise at least one thickener and/or at least one suspending agent.

Thickeners

The thickeners may be chosen from carboxyvinyl polymers; polyacrylamides; 2-acrylamido-2-methylpropanesulfonic acid polymers and copolymers, which are optionally crosslinked and/or neutralized; copolymers of 2-acrylamido-2-methylpropanesulfonic acid and of hydroxyethyl acrylate; cellulose derivatives; polysaccharides; silicas, and also cationic polymers.

Suspending Agents

The composition of the invention may also comprise one or more suspending agents, which are preferably chosen from hydrophobic modified montmorillonite clays such as hydrophobic modified bentonites or hectorites.

The suspending agents are preferably present in amounts ranging from 0.1% to 5% by weight and more preferentially from 0.2% to 2% by weight, relative to the total weight of the composition.

The amounts of these various constituents which can be present in the cosmetic composition according to the invention are those conventionally used in compositions for the treatment of perspiration.

Aerosols

The compositions according to the invention can also be pressurized and be packaged in an aerosol device made up of:

(A) a container comprising a composition as defined previously, (B) at least one propellant and one means for dispensing the said aerosol composition.

Process for Using the MIPs as Deodorant Agents

One particular embodiment of the invention relates to processes for trapping odours.

According to a particular mode of the invention, the trapping process is performed using a cosmetic composition in solution, powder, mousse, etc. form, which is deposited on the surface of the skin especially on parts with a high density of sweat glands such as the armpits.

According to a variant, after a few seconds or even minutes, the surface of the treated skin is wiped with a cloth or absorbent paper.

One particular mode of the invention concerns a trapping process which is performed at skin temperature.

The examples that follow serve to illustrate the invention without, however, being limiting in nature.

EXAMPLES

Example 1

Synthesis of MIP1 and Trapping Test

Synthesis of MIP1

| Ingredients | | Amount | Mole ratio as a function of the imprint molecule or template |
|---|---|---|---|
| Nα-hexanoylglutamine | Template molecule | 24.4 mg | 1 |
| 2-Aminoethyl methacrylate (AEM) | Functional monomer | 16.56 mg | 1 |
| Acrylamide (AAm) | Functional monomer | 28.4 mg | 4 |
| Ethylene glycol dimethacrylate (EDMA) | Crosslinking agent | 396 mg | 20 |
| Azobisdimethylvaleronitrile (ABDV) | Polymerization initiator | 10.3 mg | |
| Ethanol | Solvent (porogen) | 5 ml | |

The reagents are mixed together in the proportions and amounts defined in the above table. The polymerization is performed under an inert atmosphere (of nitrogen), thermally (preferably at 40° C.), while keeping the mixture at this temperature overnight. A "bulk" is formed. After evaporating off the solvent, a crude polymer in the form of particles is obtained. The material thus obtained is suspended with 1 M acetic acid solution for 30 minutes with stirring, and then filtered off, washed with ethanol and air-dried. 227 mg of an opaque white supple polymer in the form of particles are obtained.

The morphology of the particles is characterized using an optical microscopy machine (Morphologi G3 from the company Malvern Instruments). 2 mg of the powder are sonicated in 1 mL of water for 5 minutes and then analysed. The particles have a mean diameter of 0.97 microns and a mean circularity of 0.38.

Synthesis of the Comparative NIP1:

Non-imprinted polymers (NIPs) are synthesized in parallel to the MIPs so as to evaluate the retention power of the two materials and the MIP1 uptake selectivity relative to the NIP with regard to the imprint molecule. This starting material thus serves as a reference (non-selective starting material).

The same synthesis is performed as for MIP1 in the absence of the template to prepare a non-imprinted polymer corresponding to NIP1. 242 mg of an opaque white flexible polymer in particle form are obtained. The morphology of the particles is characterized as in example MIP1. The particles have a mean diameter of 1.45 microns and a mean circularity of 0.57.

Comparative Analysis of the Selectivity of MIP1 and NIP1 with Respect to the Odorous Molecule MIP1 or NIP1 is suspended in ethanol, under the same conditions in pairs, at varied concentrations (see FIG. 1). The analyte (Nα-hexanoylglutamine) is added at an analyte concentration of 200 µM, i.e. 200 nmol/mL. The mixture is left for 12 hours at room temperature (25° C.) and the residual amount of Nα-hexanoylglutamine not bound to the MIP1 or the NIP1 is then assayed by liquid chromatography analysis coupled to mass spectrometry (LC-MS/MS).

The "Impression Factor" (IF) of MIP1 relative to NIP1 is a known factor and is used by those skilled in the art to compare the performance qualities of MIPs. It corresponds to the amount (gram) of the odorous molecule trapped per gram of MIP1 divided by the amount (gram) of the odorous molecule trapped per gram of NIP1.

If IF>1, there is specificity for the odorous molecule.

If IF>2, there is significant and notable specificity for the odorous molecule.

The impression factor (IF) for MIP≅2 relative to NIP, which means that MIP has much better affinity for the odorous molecule (see FIG. 1).

Example 2

Synthesis of MIP2 and Trapping Test

Synthesis of MIP2

| Ingredients | | Amount | Mole ratio as a function of the imprint molecule or template |
|---|---|---|---|
| Nα-hexanoylglutamine | Template molecule | 24.4 mg | 1 |
| Methacrylic acid (MAA) | Functional monomer | 68 mg | 8 |
| Ethylene glycol dimethacrylate (EDMA) | Crosslinking agent | 396 mg | 20 |
| Azobisdimethylvaleronitrile (ABDV) | Polymerization initiator | 10.3 mg | |
| Acetonitrile | Solvent (porogen) | 7 ml | |

The reagents are mixed together in the proportions and amounts defined in the above table. The polymerization is performed under an inert atmosphere (of nitrogen), thermally (at 40° C.), while keeping the mixture at this temperature overnight with stirring. A "bulk" is formed. After evaporating off the solvent, a crude polymer in the form of particles is obtained. The material thus obtained is suspended with 1 M acetic acid solution for 30 minutes with stirring, and then filtered off, washed with ethanol and air-dried. 158 mg of an opaque white supple polymer in the form of particles are obtained. The morphology of the particles is characterized as in example MIP1. The particles have a mean diameter of 3.69 microns and a mean circularity of 0.46.

Synthesis of the Comparative NIP2:

NIP2 is synthesized under the same operating conditions and amount as for MIP2, the only difference being that the mixture does not comprise the template. 174 mg of an opaque white supple polymer in the form of particles are obtained.

The morphology of the particles is characterized as in example MIP1. The particles have a mean diameter of 1.59 microns and a mean circularity of 0.48.

Figure 2:
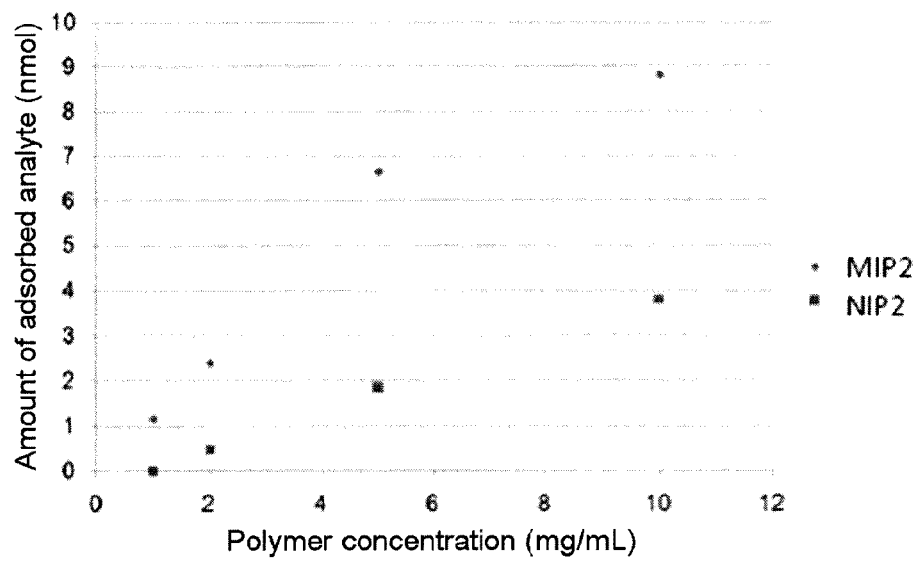

Comparative Analysis of the Selectivity of MIP2 and NIP2 with Respect to the Odorous Molecule MIP2 or NIP2 is suspended in ethanol, under the same conditions in pairs, at varied concentrations (see FIG. 2).

The analyte (Nα-hexanoylglutamine) is added at a concentration of 10 µM, i.e. 10 nmol/mL. The mixture is left for 12 hours at room temperature and the residual amount of Nα-hexanoylglutamine not bound to the MIP or the NIP is measured by LC-MS/MS.

The impression factor of MIP2 is ≅5 relative to NIP2 at 2 mg/mL of polymer and IF≅3 beyond this concentration. The results indicate strong specificity for the odorous molecule of MIP2 relative to the comparative NIP2 (see FIG. 2).

The invention claimed is:

1. A composition comprising:
   at least one molecularly imprinted polymer comprising vacant recognition sites as an agent configured to trap at least one molecule at the surface of keratin materials, wherein the at least one molecularly imprinted polymer comprising vacant recognition sites is an agent configured to trap at least one molecule chosen from odorous molecules, molecules responsible for odors, odorous molecules of the human body, molecules responsible for human body odor, molecules present in sweat, molecules present in sebum, or combinations thereof, wherein the at least one molecularly imprinted polymer is obtained by a polymerization performed in the presence of at least one template of at least one target molecule responsible for human body odour, and
   wherein at least one odorous molecule, molecule responsible for odors, imprint molecules, or templates is chosen from:
   a) branched and/or optionally substituted C2-C13 aliphatic acids of formula (T1):

   $$R^{11}-C(O)OH \tag{T1}$$

wherein in formula (T1), $R^{11}$ represents a linear or branched $(C_1$-$C_{13})$alkyl group which is optionally substituted;
   b) sulfanylalkanols or mercaptoalkanols of formula (T2):

   $$HS-R^{12}-OH \tag{T2}$$

wherein in formula (T2), $R^{12}$ represents a linear or branched $(C_1$-$C_{10})$ or $(C_1$-$C_6)$ alkylene group;
   c) the conjugated amino acids of formula (T4):

   $$R_{23}\text{-ALK-}R_{24} \tag{T4}$$

wherein in formula (T4):
      $R_{23}$ and $R_{24}$, which may be identical or different, are chosen from a $-C(X^1)-X^2-R_{25}$, $-X^2-C(X^1)-R_{25}$, $-C(X^1)-R_{25}$, wherein $X^1$ represents an oxygen atom and $X^2$ represents an NH group; $R_{25}$ is chosen from a hydrogen atom, a linear or branched $(C_1$-$C_8)$alkyl or linear or branched $(C_2$-$C_8)$alkenyl group, or methyl, optionally substituted with a hydroxyl group;
      ALK is chosen from a linear or branched $(C_1$-$C_8)$ alkylene group, optionally substituted with a group $-C(X^1)-X^2-R_{25}$, or $-X^2-C(X^1)-R_{25}$, with $R_{25}$;
   d) the acid esters of formula (T1) or the esters of formula (T'1):

   $$R^{11}-C(O)-OR'^{11} \tag{T'1}$$

wherein in formula (T'1):
$R^{11}$ represents a linear or branched $(C_1-C_{13})$alkyl group which is optionally substituted; and
$R'^{11}$ represents a methyl;
e) the conjugated products of 3-methyl-3-sulfanyl-hexan-1-ol of formula (T'4):

$$R_{25}-X^2-C(X^1)-ALK-X'^2-C(X'^1)-CH(X''^2H)-ALK'-S-R'_{25} \quad (T'4),$$

wherein in formula (T'4):
$R_{25}$ and $R'_{25}$, which may be identical or different, are chosen from a hydrogen atom, a linear or branched $(C_1-C_8)$alkyl or linear or branched $(C_2-C_8)$alkenyl group, or methyl, optionally substituted with a hydroxyl group;
ALK and ALK', which may be identical or different, represent a linear or branched $(C_1-C_8)$ alkylene group optionally substituted with a group —$X^2$—$R_{25}$, with $R_{25}$;
$X^1$ and $X^2$, which may be identical or different, representing a heteroatom chosen from oxygen, sulfur, or amino N(R") with R" being a hydrogen atom or a linear or branched $(C_1-C_6)$alkyl group;
$X'^1$ and $X'^2$, and $X''^2$, which may be identical or different, representing a heteroatom chosen from oxygen, sulfur, or amino N(R") with R" being a hydrogen atom or a linear or branched $(C_1-C_6)$alkyl group; or
f) the sulfo-conjugated steroid derivatives of formula (T3), comprising at least one sulfate group:

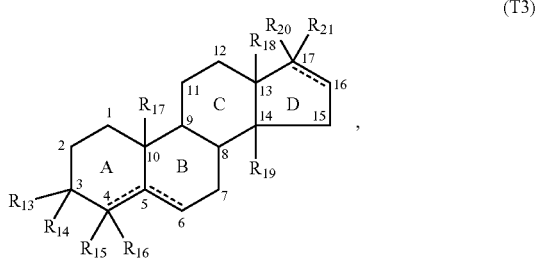

(T3)

and also optical isomers thereof, cosmetic organic or mineral acid or base salts thereof, solvates thereof, or hydrates thereof,
wherein in formula (T3):
$R_{13}$ and $R_{14}$, which may be identical or different, are chosen from a hydrogen atom or a hydroxyl group, or alternatively $R_{13}$ and $R_{14}$ form, together with the carbon atom that bears them, an oxo group;
$R_{15}$ and $R_{16}$, which may be identical or different, are chosen from a hydrogen atom, a linear or branched $(C_1-C_8)$alkyl group, methyl, or a hydroxyl group, or alternatively $R_{15}$ and $R_{16}$ form, together with the carbon atom that bears them, an oxo group, in which case the bond between carbon atoms 4 and 5 is a single bond;
═ represents a single or a double bond, with the proviso that when one of the two bonds between the two carbon atoms 4 and 5 or 5 and 6 is a double bond, then the other bond is a single bond;
$R_{17}$, $R_{18}$ and $R_{19}$, which may be identical or different, are chosen from a hydrogen atom, a linear or branched $(C_1-C_8)$alkyl group, or methyl;

$R_{20}$ and $R_{21}$, which may be identical or different, are chosen from a hydrogen atom, a linear or branched $(C_1-C_8)$alkyl group, methyl, a hydroxyl group, a group —C($X^1$)—$X^2$—$R_{22}$, —$X^2$—C($X^1$)—$R_{22}$, —C($X^1$)—$R_{22}$, with $X^1$ and $X^2$, which may be identical or different, representing a heteroatom chosen from oxygen, sulfur, or amino N(R") with R" being a hydrogen atom or a linear or branched $(C_1-C_6)$alkyl group; wherein $R_{22}$ is chosen from a hydrogen atom or a $(C_1-C_6)$alkyl group optionally substituted with a hydroxyl group, or alternatively $R_{20}$ and $R_{21}$ form, together with the carbon atom that bears them, an oxo group, in which case the bond between carbon atoms 16 and 17 is a single bond,
wherein the composition is a cosmetic composition.

2. The composition according to claim 1, further comprising a cosmetically acceptable medium.

3. The cosmetic composition according to claim 1, further comprising at least one antiperspirant active agent and/or at least one deodorant active agent other than the molecularly imprinted polymer.

4. The cosmetic composition according to claim 1, wherein the composition is present:
a) in pressurized form in an aerosol device or in a pump-dispenser bottle;
b) in a device equipped with a perforated wall;
c) in a device equipped with a ball applicator;
d) in the form of a wand; or
e) in the form of a loose or compacted powder.

5. The composition according to claim 1, wherein the at least one molecularly imprinted polymer is prepared by polymerizing a mixture in the presence of at least one template of a target molecule responsible for human body odor, the mixture comprising:
i) optionally at least one polymerization initiator;
ii) at least one functional monomer;
iii) at least one crosslinking agent; and
iv) at least one porogenic solvent.

6. The composition according to claim 1, wherein the at least one molecule is chosen from, branched, saturated, aliphatic volatile fatty acids of formula (T1), sulfanylalkanol compounds of formula (T2), or mixtures thereof.

7. The composition according to claim 1, wherein at least one odorous molecule, molecule responsible for odors, imprint molecules, or templates is chosen from:
a) branched and/or optionally substituted $C_2-C_{13}$ aliphatic acids of formula (T1):

$$R^{11}-C(O)-OH \quad (T1),$$

wherein in formula (T1), $R^{11}$ represents a linear or branched $(C_1-C_{13})$alkyl group which is optionally substituted.

8. The composition according to claim 1, wherein at least one odorous molecule, molecule responsible for odors, imprint molecules, or templates is chosen from:
b) sulfanylalkanols or mercaptoalkanols of formula (T2):

$$HS-R^{12}-OH \quad (T2),$$

wherein in formula (T2), $R^{12}$ represents a linear or branched $(C_1-C_{10})$ or $(C_1-C_6)$ alkylene group.

9. The composition according to claim 1, wherein at least one odorous molecule, molecule responsible for odors, imprint molecules, or templates is chosen from:
c) the conjugated amino acids of formula (T4):

$$R_{23}\text{-ALK-}R_{24} \quad (T4),$$

wherein in formula (T4):

R₂₃ and R₂₄, which may be identical or different, are chosen from a —C(X¹)—X²—R₂₅, —X²—C(X¹)—R₂₅, —C(X¹)—R₂₅, wherein X¹ represents an oxygen atom and X² represents an NH group; R₂₅ is chosen from a hydrogen atom, a linear or branched (C₁-C₈)alkyl or linear or branched (C₂-C₈)alkenyl group, or methyl, optionally substituted with a hydroxyl group;

ALK is chosen from a linear or branched (C₁-C₈) alkylene group, optionally substituted with a group —C(X¹)—X²—R₂₅, or —X²—C(X¹)—R₂₅, with R₂₅.

10. The composition according to claim 1, wherein at least one odorous molecule, molecule responsible for odors, imprint molecules, or templates is chosen from:

d) the acid esters of formula (T1) or the esters of formula (Ti):

R¹¹—C(O)—OR'¹¹      (T'1), wherein in formula (Ti):

R¹¹ represents a linear or branched (C₁-C₁₃)alkyl group which is optionally substituted; and R'¹¹ represents a methyl.

11. The composition according to claim 1, wherein at least one odorous molecule, molecule responsible for odors, imprint molecules, or templates is chosen from:

e) the conjugated products of 3-methyl-3-sulfanylhexan-1-ol of formula (T'4):

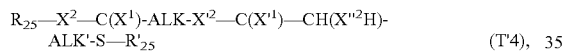

R₂₅—X²—C(X¹)-ALK-X'²—C(X'¹)—CH(X"²H)-ALK'-S—R'₂₅      (T'4), wherein in formula (T'4):

R₂₅ and R'₂₅, which may be identical or different, are chosen from a hydrogen atom, a linear or branched (C₁-C₈)alkyl or linear or branched (C₂-C₈)alkenyl group, or methyl, optionally substituted with a hydroxyl group;

ALK and ALK', which may be identical or different, represent a linear or branched (C₁-C₈)alkylene group optionally substituted with a group —X²—R₂₅, with R₂₅;

X¹ and X², which may be identical or different, representing a heteroatom chosen from oxygen, sulfur, or amino N(R") with R" being a hydrogen atom or a linear or branched (C₁-C₆)alkyl group;

X'¹ and X'², and X"², which may be identical or different, representing a heteroatom chosen from oxygen, sulfur, or amino N(R") with R" being a hydrogen atom or a linear or branched (C₁-C₆) alkyl group.

12. The composition according to claim 1, wherein at least one odorous molecule, molecule responsible for odors, imprint molecules, or templates is chosen from:

f) the sulfo-conjugated steroid derivatives of formula (T3), comprising at least one sulfate group:

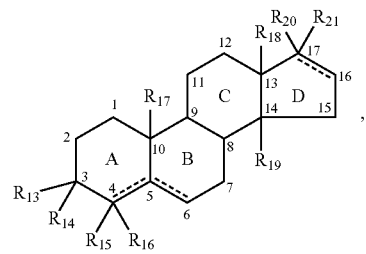

(T3)

and also optical isomers thereof, cosmetic organic or mineral acid or base salts thereof, solvates thereof, or hydrates thereof, wherein in formula (T3):

R₁₃ and R₁₄, which may be identical or different, are chosen from a hydrogen atom or a hydroxyl group, or alternatively R₁₃ and R₁₄ form, together with the carbon atom that bears them, an oxo group;

R₁₅ and R₁₆, which may be identical or different, are chosen from a hydrogen atom, a linear or branched (C₁-C₈)alkyl group, methyl, or a hydroxyl group, or alternatively R₁₅ and R₁₆ form, together with the carbon atom that bears them, an oxo group, in which case the bond between carbon atoms 4 and 5 is a single bond;

= represents a single or a double bond, with the proviso that when one of the two bonds between the two carbon atoms 4 and 5 or 5 and 6 is a double bond, then the other bond is a single bond;

R₁₇, R₁₈ and R₁₉, which may be identical or different, are chosen from a hydrogen atom, a linear or branched (C₁-C₈)alkyl group, or methyl;

R₂₀ and R₂₁, which may be identical or different, are chosen from a hydrogen atom, a linear or branched (C₁-C₈)alkyl group, methyl, a hydroxyl group, a group —C(X¹)—X²—R₂₂, —X²—C(X¹)—R₂₂, —C(X¹)—R₂₂, with X¹ and X², which may be identical or different, representing a heteroatom chosen from oxygen, sulfur, or amino N(R") with R" being a hydrogen atom or a linear or branched (C₁-C₆)alkyl group; wherein R₂₂ is chosen from a hydrogen atom or a (C₁-C₆)alkyl group optionally substituted with a hydroxyl group, or alternatively R₂₀ and R₂₁ form, together with the carbon atom that bears them, an oxo group, in which case the bond between carbon atoms 16 and 17 is a single bond.

13. The composition according to claim 1, wherein the composition is present in pressurized form in an aerosol device or in a pump-dispenser bottle.

14. The composition according to claim 1, wherein the composition is present in a device equipped with a perforated wall.

15. The composition according to claim 1, wherein the composition is present in a device equipped with a ball applicator.

16. The composition according to claim 1, wherein the composition is in the form of a wand.

17. The composition according to claim 1, wherein the composition is in the form of a loose or compacted powder.

* * * * *

UNITED STATES PATENT AND TRADEMARK OFFICE
CERTIFICATE OF CORRECTION

| | |
|---|---|
| PATENT NO. | : 10,772,823 B2 |
| APPLICATION NO. | : 14/655390 |
| DATED | : September 15, 2020 |
| INVENTOR(S) | : Andrew Greaves et al. |

It is certified that error appears in the above-identified patent and that said Letters Patent is hereby corrected as shown below:

In the Claims

Claim 10, Column 51, Line 19, please change "Ti" to -- T'i --; and

Claim 10, Column 51, Line 21, please change "Ti" to -- T'1 --.

Signed and Sealed this
Twelfth Day of July, 2022

Katherine Kelly Vidal
*Director of the United States Patent and Trademark Office*